(12) United States Patent
Wildhaber et al.

(10) Patent No.: US 11,712,181 B2
(45) Date of Patent: Aug. 1, 2023

(54) SYSTEM FOR COLLECTION AND ANALYSIS OF BIOFLUID FROM SKIN AND METHOD OF USING THE SAME

(71) Applicant: Xsensio SA, Lausanne (CH)

(72) Inventors: Fabien Patrick Wildhaber, Troistorrents (CH); Neil Ebejer, Lausanne (CH); Hoël Maxime Guérin, Lausanne (CH); Johan Frédéric Longo, Lausanne (CH)

(73) Assignee: Xsensio SA, Lausanne (CH)

( * ) Notice: Subject to any disclaimer, the term of this patent is extended or adjusted under 35 U.S.C. 154(b) by 326 days.

(21) Appl. No.: 16/975,690

(22) PCT Filed: Mar. 6, 2019

(86) PCT No.: PCT/EP2019/055616
§ 371 (c)(1),
(2) Date: Aug. 25, 2020

(87) PCT Pub. No.: WO2019/170776
PCT Pub. Date: Sep. 12, 2019

(65) Prior Publication Data
US 2020/0397352 A1 Dec. 24, 2020

Related U.S. Application Data

(60) Provisional application No. 62/641,157, filed on Mar. 9, 2018, provisional application No. 62/639,418, filed on Mar. 6, 2018.

(51) Int. Cl.
A61B 5/145 (2006.01)
A61B 5/01 (2006.01)
A61B 5/00 (2006.01)

(52) U.S. Cl.
CPC ............ *A61B 5/14517* (2013.01); *A61B 5/01* (2013.01); *A61B 5/4266* (2013.01);
(Continued)

(58) Field of Classification Search
CPC ..... A61B 5/14517; A61B 5/01; A61B 5/4266; A61B 5/6813; A61B 2562/0214;
(Continued)

(56) References Cited

U.S. PATENT DOCUMENTS 6,616,823 B2 9/2003 Kopf-Sill
9,116,145 B2 8/2015 Li et al.
(Continued)

FOREIGN PATENT DOCUMENTS

WO WO-2010/045247 A1 4/2010
WO WO-2012/050873 A2 4/2012
(Continued)

OTHER PUBLICATIONS

C. Huang et al., A Capillary-Driven Microfluidic Device for Rapid DNA Detection with Extremely Low Sample Consumption, 17th International Conference on Miniaturized Systems for Chemistry and Life Sciences, 191-93, 2013 (Year: 2013).*
(Continued)

*Primary Examiner* — Eric F Winakur
*Assistant Examiner* — Jonathan Drew Moroneso
(74) *Attorney, Agent, or Firm* — Choate, Hall & Stewart LLP; William R. Haulbrook; Michael D. Schmitt

(57) ABSTRACT

Presented herein are systems, methods for collecting fluid from a surface (e.g., skin) and analyzing the fluid (e.g., to measure chemical, physical and/or biological properties of the fluid). For example, a system for fluid collection on a surface (e.g., skin) and fluid analysis includes at least one of the following modules: (i) a collection and delivery module to collect a fluid over a wet or partially wet surface and
(Continued)

deliver it to (ii) a main sensing module to perform chemical, physical and/or biological analysis on the fluid. The system also includes (iii) a flow regulation module, for controlling fluid flow (e.g., transport) through the system and (iv) a waste module to collect and/or dispose of the fluid after analysis is complete.

22 Claims, 26 Drawing Sheets

(52) U.S. Cl.
CPC .... *A61B 5/6813* (2013.01); *A61B 2562/0214* (2013.01); *A61B 2562/0247* (2013.01); *A61B 2562/0271* (2013.01)

(58) Field of Classification Search
CPC .... A61B 2562/0247; A61B 2562/0271; A61B 2562/029; A61B 5/441; A61B 10/0064; A61B 5/14546; G16H 50/30
See application file for complete search history.

(56) References Cited

U.S. PATENT DOCUMENTS

| | | | |
|---|---|---|---|
| 9,810,660 | B2 | 11/2017 | Hu et al. |
| 10,653,342 | B2 | 5/2020 | Rogers et al. |
| 10,925,523 | B2 | 2/2021 | Rogers et al. |
| 11,331,009 | B2 | 5/2022 | Ionescu et al. |
| 2002/0049389 | A1 | 4/2002 | Abreu |
| 2004/0096959 | A1* | 5/2004 | Stiene .............. A61B 5/150755 435/287.2 |
| 2004/0129678 | A1 | 7/2004 | Crowley et al. |
| 2007/0027383 | A1 | 2/2007 | Peyser et al. |
| 2010/0112723 | A1* | 5/2010 | Battrell ............. B01L 3/502746 422/68.1 |
| 2015/0314288 | A1* | 11/2015 | Prins .................. B01L 3/50273 436/501 |
| 2016/0287164 | A1* | 10/2016 | Manion ................ A61B 5/4266 |
| 2017/0100102 | A1* | 4/2017 | Heikenfeld ........ A61B 5/14521 |
| 2017/0212098 | A1* | 7/2017 | Stolovitzky ....... B01L 3/502761 |
| 2017/0231571 | A1 | 8/2017 | Rogers et al. |
| 2018/0020966 | A1 | 1/2018 | Begtrup et al. |
| 2018/0064377 | A1 | 3/2018 | Rogers et al. |
| 2018/0153451 | A1 | 6/2018 | Heikenfeld et al. |
| 2018/0199866 | A1* | 7/2018 | Heikenfeld ........ A61B 5/14517 |
| 2018/0289296 | A1* | 10/2018 | Heikenfeld .......... A61B 5/6833 |
| 2019/0110722 | A1 | 4/2019 | Ionescu et al. |
| 2019/0183398 | A1 | 6/2019 | Heikenfeld et al. |
| 2019/0191998 | A1 | 6/2019 | Heikenfeld et al. |
| 2019/0191999 | A1 | 6/2019 | Heikenfeld et al. |
| 2019/0192000 | A1 | 6/2019 | Heikenfeld et al. |
| 2020/0077988 | A1 | 3/2020 | Heikenfeld |
| 2020/0155046 | A1* | 5/2020 | Beech ....................... A61B 5/01 |
| 2020/0315503 | A1 | 10/2020 | Heikenfeld et al. |
| 2021/0369490 | A1* | 12/2021 | Hansen ................ A61B 5/4851 |
| 2021/0381921 | A1* | 12/2021 | Beguin .................... G01M 3/16 |
| 2022/0401012 | A1 | 12/2022 | Wildhaber et al. |

FOREIGN PATENT DOCUMENTS

| | | | | |
|---|---|---|---|---|
| WO | WO-2016/030869 | A1 | | 3/2016 |
| WO | WO-2017/019573 | A1 | | 2/2017 |
| WO | WO-2017019573 | A1 * | 2/2017 | ......... A61B 5/14517 |
| WO | WO-2018/047125 | A1 | | 3/2018 |
| WO | WO-2018/223090 | A1 | | 12/2018 |
| WO | WO-2019/060689 | A1 | | 3/2019 |
| WO | WO-2019/170776 | A1 | | 9/2019 |
| WO | WO-2021/099610 | A1 | | 5/2021 |

OTHER PUBLICATIONS

Lin Yang et al., The Frequency Spectral Properties of Electrode-Skin Contact Impedance on Human Head and Its Frequency-Dependent Effects on Frequency-Difference EIT in Stroke Detection from 10Hz to 1MHz, PLOS ONE, 1-21, 2017 (Year: 2017).*
Olanrewaju et al., "Capillary microfluidics in microchannels: from microfluidic networks to capillaric circuits", Lab Chip, 18, 2323-2347, published Jul. 16, 2018 (Year: 2018).*
Craighead, H., Future lab-on-a-chip technologies for interrogating individual molecules, Nature, (Jul. 27, 2006), 442:387-393, (2006).
Gao, W. et al., A. Javey, Fully integrated wearable sensor arrays for multiplexed in situ perspiration analysis, Nature, 529(7587):509-514, (2016).
Heikenfeld, J., Non-invasive Analyte Access and Sensing through Eccrine Sweat: Challenges and Outlook circa, , 28(6):1242-1249, (2016).
International Search Report, Application No. PCT/EP2015/055616 (System for Collection and Analysis of Biofluid From Skin and Method of Using the Same, filed Mar. 6, 2019), issued by ISA/ European Patent Office, 4 pages, dated May 16, 2019.
Morak; Jurgen et al., Design and evaluation of a telemonitoring concept based on NFC-enabled mobile phones and sensor devices, IEEE transactions on information technology in biomedicine, (20120000), 16.1:17-23.
Written Opinion, International Application No. PCT/EP2015/ 055616 (System for Collection and Analysis of Biofluid From Skin and Method of Using the Same, filed Mar. 6, 2019), issued by ISA/European Patent Office, 8 pages, dated May 16, 2019.

* cited by examiner

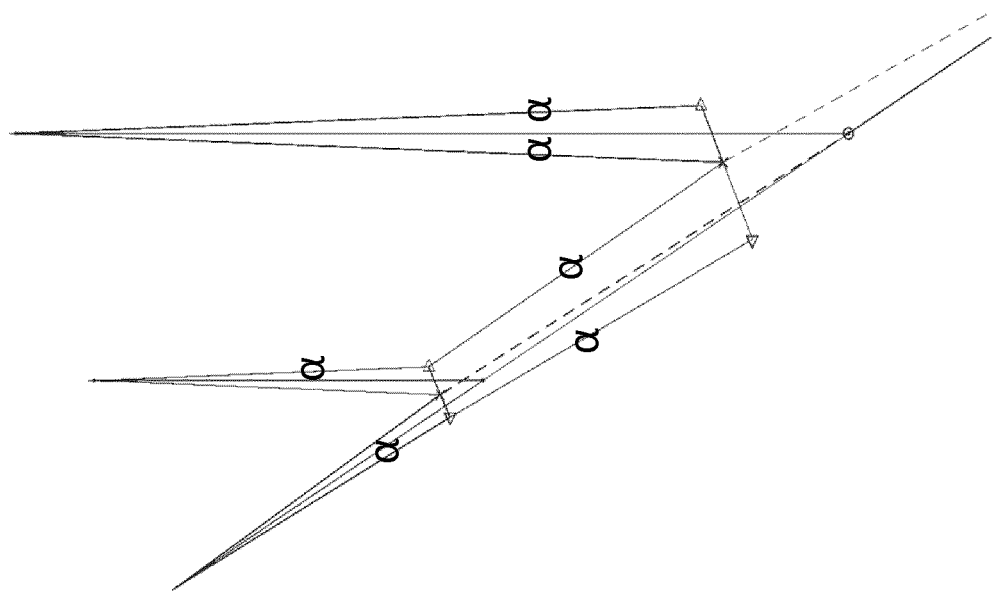
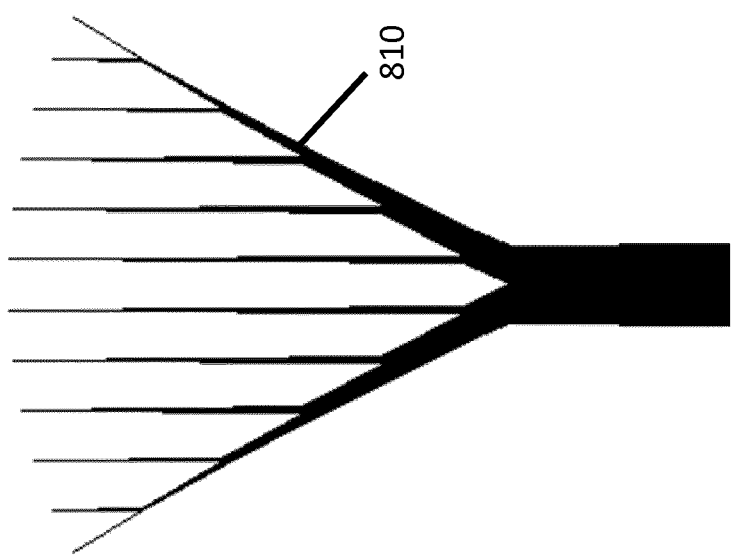
Fig. 10

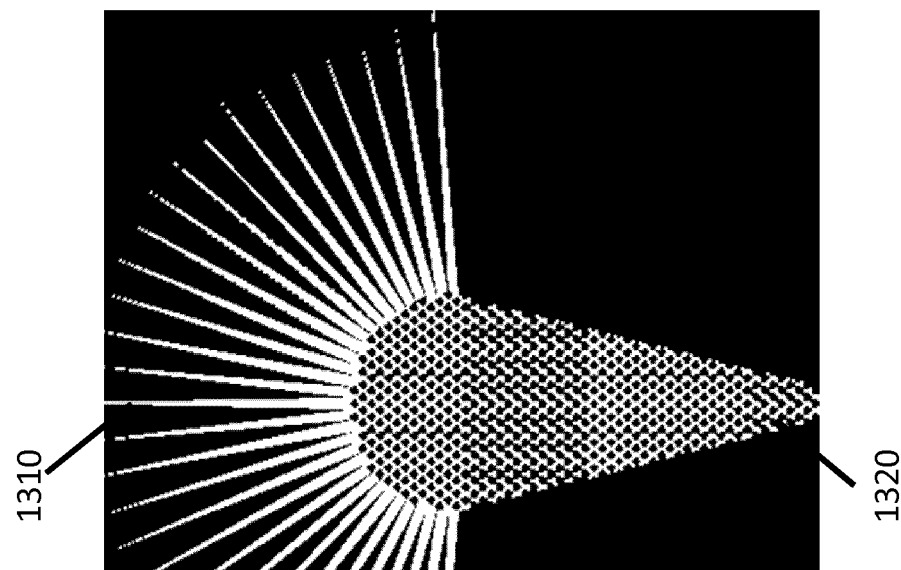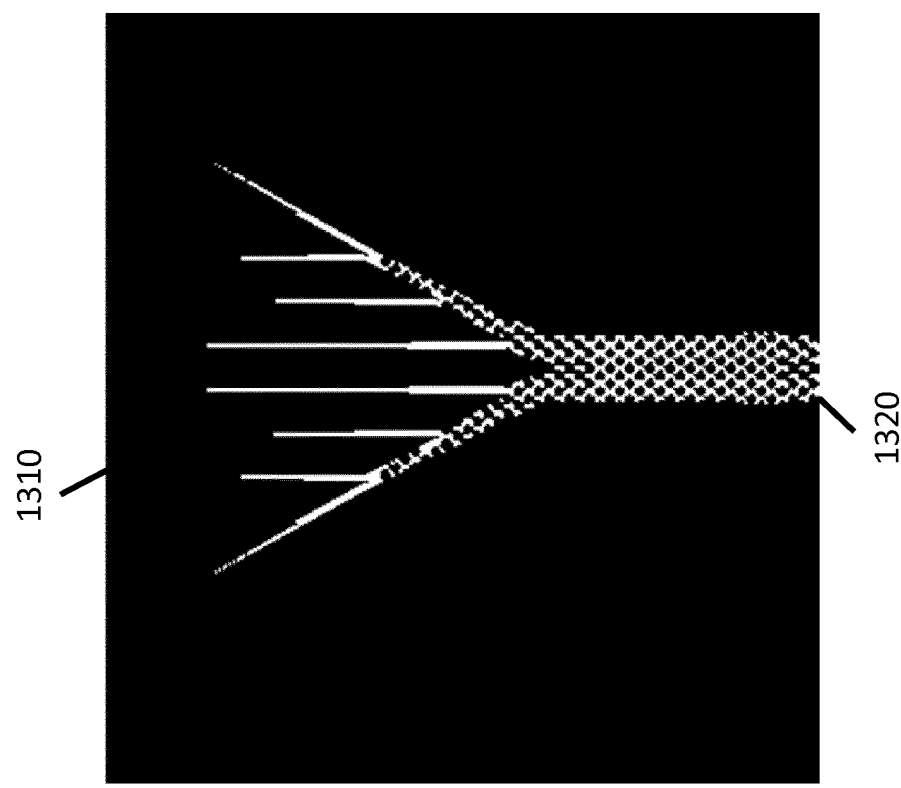
Fig. 13

SYSTEM FOR COLLECTION AND ANALYSIS OF BIOFLUID FROM SKIN AND METHOD OF USING THE SAME

CROSS-REFERENCE TO RELATED APPLICATIONS

This application is a national stage entry, under 35 U.S.C. § 371, of International (PCT) Application No. PCT/EP2019/055616, filed Mar. 6, 2019, which claims priority to and the benefit of U.S. Provisional Patent Application No. 62/639,418, filed Mar. 6, 2018, and U.S. Provisional Patent Application No. 62/641,157, filed Mar. 9, 2018, the contents of which are incorporated by reference herein in their entirety.

FIELD OF THE INVENTION

This invention relates generally to systems and methods for collecting and analyzing biofluids. In certain embodiments, the invention relates to a wearable device for the collection and analysis of biofluids from the skin of a user.

BACKGROUND OF THE INVENTION

A biomarker is a measurable substance in an organism. The presence and/or quantity of a biomarker in a biofluid of the organism is indicative of some phenomenon and/or characteristic of the organism such as a disease, an infection, an environmental exposure (e.g., to a chemical), or state of being (e.g., a level of stress). Examples of commonly measured biomarkers in humans include proteins, hormones, metabolites, and ions. For example, glucose is a biomarker that is typically measured in the blood of diabetic individuals to help them manage their disease.

Biomarkers are often measured in blood. Acquiring blood samples is invasive and can cause significant discomfort to the individual's being tested. Typical strategies of biomarker analysis involve obtaining a blood sample from a person and performing a test (e.g., for biomarker detection and/or quantification) in a laboratory. This process is slow, expensive, and limited to a single sampling moment in time. Using existing techniques, each blood sample that is obtained often must be stored and transported to an appropriate laboratory where biomarker analysis can be performed by specially trained technicians using specialized equipment. This sequence of steps adds to the cost (e.g., of laboratory equipment and technician time) and time (e.g., for transport and manual analysis) required for biomarker analysis. Biomarker analysis, from the time of sample collection to the time results reach an individual being tested (e.g., a patient), commonly takes hours, days, or longer before results are available.

Since existing technology for measuring biomarkers only provides biomarker analysis data at discrete time points, biomarkers cannot be effectively measured continuously or in real-time. If frequent biomarker measurements are needed (e.g., several measurements per hour), many blood samples must be acquired from the individual being tested, leading to a significant increase in discomfort and inconvenience.

There is thus a need for improved systems and methods for continuous, non-invasive detection and/or quantification of biomarkers in biofluids.

SUMMARY OF THE INVENTION

Presented herein are systems and methods for collecting fluid from a surface (e.g., skin) and analyzing the fluid (e.g., to measure chemical, physical and/or biological properties of the fluid). For example, a system for fluid collection on a surface (e.g., skin) and fluid analysis includes the following modules: (i) a collection and delivery module to collect a fluid over a wet or partially wet surface and deliver it to (ii) a main sensing module to perform chemical, physical and/or biological analysis on the fluid. The system also includes (iii) a flow regulation module, for controlling fluid flow (e.g., transport) through the system and (iv) a waste module to collect and/or dispose of the fluid after analysis is complete.

In certain embodiments, the system also includes (v) a wetting sensor module based on conductivity measurements, which are used to determine whether some or all of the above-mentioned modules are wet (e.g., exposed to a liquid) and to provide an estimate of the flow rate as the system is filled. In certain embodiments, the system also includes (vi) a module to chemically activate a sensor (e.g., a single time or repeatedly) using a dedicated fluid delivery system. In certain embodiments, each of modules (i)-(iv) and optional modules (v) and (vi) are integrated within one microchip or an assembly of microchips. For example, the modules may be mounted on a printed circuit board (e.g., a flexible printed circuit board) and/or embedded within an electronic device (e.g., in an adhesive patch or in a wearable device (e.g., a wrist-band, a head-band, a bandage, a sock, a glove, an arm-band, a waist-band, an ankle-band, and a knee-band).

In one aspect, the present disclosure is directed to a system for collection and analysis of a fluid (e.g., a biofluid, e.g., sweat) from a surface (e.g., skin of a user), the system comprising: a collection and delivery module to collect a fluid from a wet (e.g., or semi-wet) surface (e.g., skin of a human); a sensing module to determine (e.g., detect and/or quantify) one or more chemical and/or physical properties of the fluid [e.g., wherein the sensing module comprises at least one sensor (e.g., a chemical sensor, e.g., a temperature sensor, e.g., a conductivity sensor, e.g., a pressure sensor, e.g., a flow rate sensor)]; a flow regulation module; and a waste module.

In certain embodiments, the system comprises a wetting sensor module, wherein the wetting sensor module comprises one or more conductivity sensors (e.g., one or more platinum or Ag/AgCl electrodes for measuring conductivity).

In certain embodiments, the system comprises a chemical activation module for chemically activating the sensor, wherein the chemical activation module comprises a fluid delivery system for chemically activating the sensor (e.g., once or repeatedly).

In certain embodiments, the system comprises a microchip assembly for integrating at least one module selected from the group consisting of the collection and delivery module, the sensing module, the flow regulation module, the waste module, the (optional) wetting sensor module, and the (optional) chemical activation module, wherein the microchip assembly comprises a printed circuit board (e.g., a flexible printed circuit board) or a wearable device (e.g., a wrist-band, a head-band, a bandage, a sock, a glove, an arm-band, a waist-band, an ankle-band, and a knee-band).

In certain embodiments, the collection and delivery module comprises a collection surface, one or more collection structures, and/or one or more inlets (e.g., and a sealant material, e.g., and a spacer layer, e.g., and a filter) (e.g., for collecting a volume of the fluid from a collection zone) [e.g., for collecting a volume of the fluid from a collection zone (e.g., a region of a skin surface)].

In certain embodiments, the collection structures comprise at least one fluidic channel or a fluidic channel network (e.g., an arborescent channel network).

In certain embodiments, the at least one fluidic channel or fluidic channel network comprises a member selected from the group consisting of a groove, an open or closed microfluidic channel, a two-dimensional channel defined by surface property contrast, and a channel made of a fixed gel matrix permeable to a fluid.

In certain embodiments, the fluidic channel or fluidic channel network comprises an open channel and/or a closed channel.

In certain embodiments, each of the at least one fluidic channel or fluidic channel network is modified (e.g., using a hydrogel, e.g., using oxygen plasma, e.g., by functionalizing and/or grafting a functional molecule to one or more surfaces of the at least one fluidic channel or the fluidic channel network).

In certain embodiments, a portion of the at least one fluidic channel or fluidic channel network comprises pillar structures (e.g., and/or pavement structures) (e.g., or arrays thereof) to reduce dead volume and/or facilitate fluid transport via capillary action (e.g., and/or to filter the fluid).

In certain embodiments, the pillar structures comprise a size gradient in one direction to promote directional flow. In certain embodiments, the pillar structures comprise an interstitial distance gradient in one direction to promote directional flow.

In certain embodiments, the at least one fluidic channel or fluidic channel network comprises a filter to exclude a contaminant. In certain embodiments, the filter comprises a member selected from the group consisting of an array of pillar structures, a fiber matrix, and a gel matrix. In certain embodiments, the contaminant comprises a member selected from the group consisting of lipids, bacteria, particles, and dead skin cells.

In certain embodiments, the system comprises a sealant material surrounding the inlet.

In certain embodiments, the sealant material acts as a spacer layer.

In certain embodiments, the sealant material is semipermeable. In certain embodiments, the sealant material is impermeable to liquid. In certain embodiments, the sealant material is permeable to air.

In certain embodiments, the sealant material comprises one or more members selected from the group consisting of an elastomer, a gel, a grease, a glue (e.g., silicone or acrylate glue), an adhesive, and a laminate (e.g., an adhesive trilaminate). In certain embodiments, the sensing module comprises at least one sensor (e.g., a chemical sensor, e.g., a temperature sensor, e.g., a conductivity sensor, e.g., a pressure sensor, e.g., a flow rate sensor) for measuring one or more chemical and/or physical properties of the fluid (e.g., and one or more reference sensors).

In certain embodiments, the one or more chemical and/or physical properties of the fluid comprise one or more members selected from the group consisting of: a concentration of one or more substances present in the fluid, a pH of the fluid, a conductivity of the fluid, a temperature of the fluid and/or the surface, a pressure of the fluid, and a flow rate (e.g., flow velocity) of the fluid [e.g., wherein the one or more substances include one or more members selected from the group consisting of ions (e.g., chloride, sodium, potassium), sugars (e.g., glucose), and biomolecules (e.g., polynucleotides, proteins, hormones, enzymes, antigens, neuropeptides, antibodies) (e.g., and any solute)].

In certain embodiments, the at least one sensor comprises one or more members selected from the group consisting of an electrode, a capacitor (e.g., a MOSCAP), a transistor (e.g., an ISFET), a conductivity sensor, a temperature sensor (e.g., a thermocouple, a thermistor, a diode-based temperature sensor, or a resistance temperature detector (RTD)), a pressure sensor (e.g., gauge-based pressure sensor, e.g., a MEMS based pressure sensor, e.g., a piezoresistive pressure sensor), and a flow rate sensor.

In certain embodiments, a surface of one or more of the at least one sensor is functionalized to detect a specific substance (e.g., wherein the functionalized surface comprises a thin film, a plurality of functional molecules, and/or a functional membrane)

In certain embodiments, the sensing module comprises one or more reference devices for obtaining differential measurements.

In certain embodiments, the sensing module comprises one or more reference electrodes (e.g., a Ag/AgCl electrode).

In certain embodiments, the sensing module comprises a polymer layer disposed on top of the at least one sensor.

In certain embodiments, the flow regulation module comprises one or more members selected from the group consisting of: a capillary pump [e.g., comprising an array of pillars or pavements and/or a wicking or absorbent material (e.g., a paper or a textile)], a patterned surface [e.g., with a particular surface property (e.g., surface energy)], a barrier (e.g., a hydrophobic zone for flow of a water-based solution), and/or a fluidic valve.

In certain embodiments, the flow regulation module is a passive flow regulation module comprising an overflow device.

In certain embodiments, the overflow device comprises a surface property barrier, and/or a capillary pump.

In certain embodiments, the flow regulation module is an active flow regulation module comprising an actuated fluidic valve (e.g., a mechanical valve, a pneumatic valve, an electronic valve, or an electroosmotic valve).

In certain embodiments, the flow regulation module is positioned between the sensor module and the waste module.

In certain embodiments, the flow regulation module is positioned between the collection and delivery module and the sensor module (e.g., or embedded within the sensor module).

In certain embodiments, the waste module comprises a capillary pump (e.g., an array of pillars (e.g. hexagonal pillars) or pavements and/or a wicking material based for instance on a paper, a textile, a gel or an absorbent material] and a waste reservoir (e.g., an absorbent pad for collecting waste) (e.g., wherein each pillar of the array of pillars has a width of between 1 μm to 1 mm and is separated from neighboring pillars by a distance of 1 μm to 1 mm) (e.g., wherein the array of pillars is a regular array, e.g., wherein the array of pillars is an irregular array).

In certain embodiments, the conductivity sensor comprises one or more electrodes.

In certain embodiments, the one or more electrodes comprises a noble metal. In certain embodiments, the one or more electrodes are actuated by an AC signal in a frequency range of about 1 kHz to about 100 kHz. In certain embodiments, the one or more electrodes are actuated by a DC signal.

In certain embodiments, the chemical activation module comprises one or more members selected from the group consisting of: a fluidic inlet for loading a chemical solution, a fluidic reservoir to store the chemical solution, a dedicated delivery fluidic channel or fluidic channel network to transport the chemical solution, and a flow regulation module.

In certain embodiments, the microchip assembly comprises a processor to perform computations and a memory to store results of the computations.

In certain embodiments, the collection structures comprise an arborescent channel network, wherein the arborescent channel network comprises a plurality of branched channels.

In certain embodiments, the collection surface has a surface area of 10 mm$^2$ or greater.

In certain embodiments, the at least one fluidic channel or the fluidic channel network comprises a fluidic channel with a width in a range from about 1 µm to about 1 mm and/or a height in a range from about 50 µm to about 1 mm.

In certain embodiments, the collection and delivery module comprises a spacer layer, wherein the spacer layer has a thickness in a range from about 10 µm to about 500 µm.

BRIEF DESCRIPTION OF THE DRAWINGS

The foregoing and other objects, aspects, features, and advantages of the present disclosure will become more apparent and better understood by referring to the following description taken in conjunction with the accompanying drawings, in which:

FIG. 10 is a schematic diagram showing arborescent collection structures with constant angle, according to an illustrative embodiment.

FIG. 13 is a schematic diagram showing hybrid collection structures, according to an illustrative embodiment.

Figure 1:
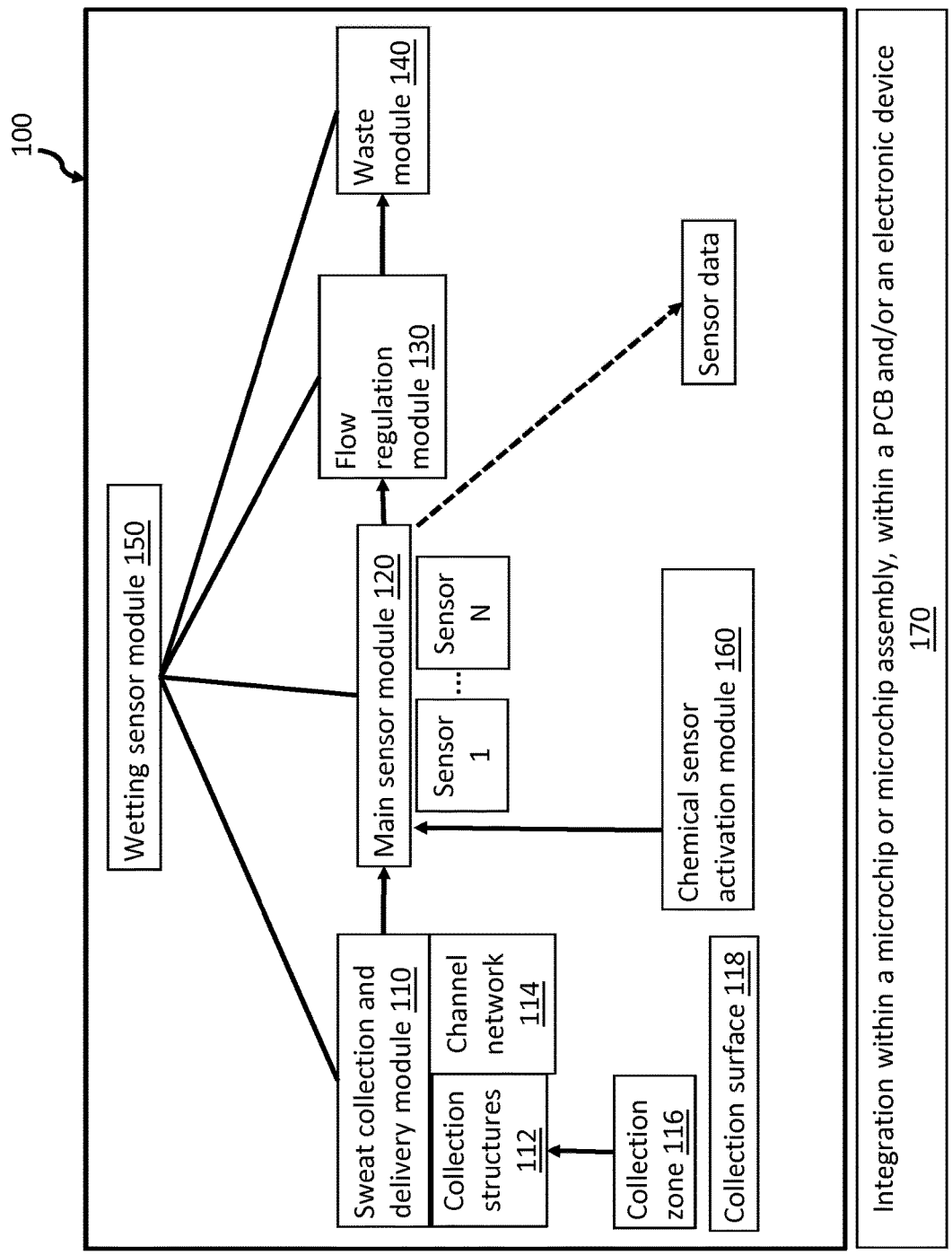
FIG. 1 is a block diagram of a system for collection and analysis of a fluid (e.g., a biofluid, e.g., sweat) from a surface (e.g., skin of a user), according to an illustrative embodiment.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION

It is contemplated that systems, architectures, devices, methods, and processes of the claimed invention encompass variations and adaptations developed using information from the embodiments described herein. Adaptation and/or modification of the systems, architectures, devices, methods, and processes described herein may be performed, as contemplated by this description.

Throughout the description, where articles, devices, systems, and architectures are described as having, including, or comprising specific components, or where processes and methods are described as having, including, or comprising specific steps, it is contemplated that, additionally, there are articles, devices, systems, and architectures of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

Elements of embodiments described with respect to a given aspect of the invention may be used in various embodiments of another aspect of the invention. For example, it is contemplated that features of dependent claims depending from one independent claim can be used in apparatus, articles, systems, and/or methods of any of the other independent claims.

The mention herein of any publication, for example, in the Background section, is not an admission that the publication serves as prior art with respect to any of the claims presented herein. The Background section is presented for purposes of clarity and is not meant as a description of prior art with respect to any claim.

Documents are incorporated herein by reference as noted. Where there is any discrepancy in the meaning of a particular term, the meaning provided in the Definition section above is controlling.

Headers are provided for the convenience of the reader. The presence and/or placement of a header is not intended to limit the scope of the subject matter described herein.

As used herein, unless otherwise clear from context, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) where ranges are provided, endpoints are included.

As used herein, the terms "about" or "approximately", when used herein in reference to a value, refers to a value that is similar, in context to a referenced value. In general, those skilled in the art, familiar with the context, will appreciate the relevant degree of variance encompassed by "about" or "approximately" in that context. For example, in some embodiments, the terms "about" or "approximately" may encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referred value.

As used herein, the term "continuous," as in a continuous biomarker measurement, refers to performing a series of measurements (e.g., of the presence and/or quantity of a biomarker) without a substantial time interval between each measurement. For example, continuous measurements may be performed at a rate of one measurement every ten minutes, one measurement every five minutes, one measurement per minute, one measurement every 30 seconds, one measurement every 5 seconds, or faster rates.

In certain embodiments, a continuous measurement can occur in substantially "real-time" such that the concentration value of an analyte measured by the device is the concentration present in sweat without a substantial delay or latency on the timescale of physiological processes (e.g., on a scale of five minute or greater). For example, the device may display a "snapshot" of the concentration of an analyte in the biofluid (e.g., every 5 minutes, 1 minute, 30 seconds or less). In certain embodiments, the continuous measurements are performed at a higher frequency (e.g., every second or every several milliseconds) providing a continuous analyte data stream faster than the physiological timescale.

As used herein, the term "substantially" refers to the qualitative condition of exhibiting total or near-total extent or degree of a characteristic or property. For example, a substantially constant value may vary in time by 20%, 15%, 10%, 9%, 8%, 7%, 6%, 5%, 4%, 3%, 2%, 1%, or less of the constant value.

Presented herein are systems, methods for collecting fluid from a surface (e.g., skin) and analyzing the fluid (e.g., to measure chemical, physical and/or biological properties of the fluid). In certain embodiments, as shown in FIG. 1, a system 100 for fluid collection on a surface (e.g., skin) and fluid analysis includes at least one of the following modules: a collection and delivery module 110 to collect a fluid over a wet or partially wet surface and deliver it to a main sensor module 120 to perform chemical, physical and/or biological analysis on the fluid. The system also includes a flow regulation module 130, for controlling fluid flow (e.g., transport) through the system and a waste module 140 to collect and/or dispose of the fluid after analysis is complete.

In certain embodiments, system 100 includes a wetting sensor module 150 based on conductivity measurements, which are used to determine whether some or all of the above-mentioned modules are wet (e.g., exposed to a liquid) and to provide an estimate of the flow rate as the system is filled. In certain embodiments, the system includes a module 160 to chemically activate a sensor (e.g., a single time or repeatedly) using a dedicated fluid delivery system. In certain embodiments, each of modules 110, 120, 130 and 140 and optional modules 150 and 160 are integrated within one microchip or an assembly of microchips. System 100 can be disposed on a substrate 220 which can provides mechanic support and electrical connections to system 100. In certain embodiments, substrate 220 includes a printed circuit board, a polymer substrate (e.g., plastic), or a metal substrate. For example, the modules may be mounted on a printed circuit board (e.g., a flexible printed circuit board) and/or embedded within an electronic device (e.g., in an adhesive patch or in a wearable device (e.g., a wrist-band, a head-band, a bandage, a sock, a glove, an arm-band, a waist-band, an ankle-band, and a knee-band).

Figure 2:
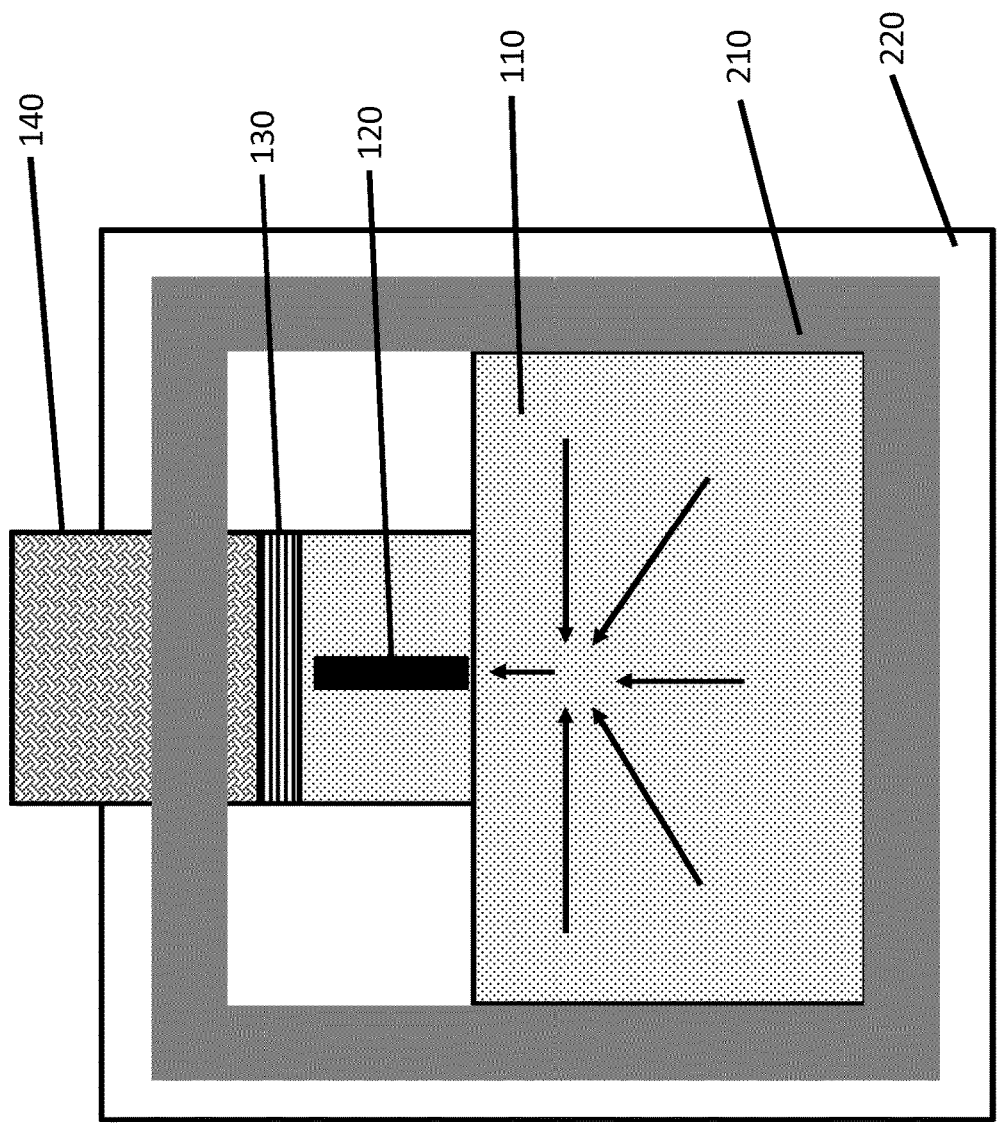
FIG. 2 is a schematic diagram showing a top view of a system for collection and analysis of a fluid from a surface, according to an illustrative embodiment.
Figure 3:
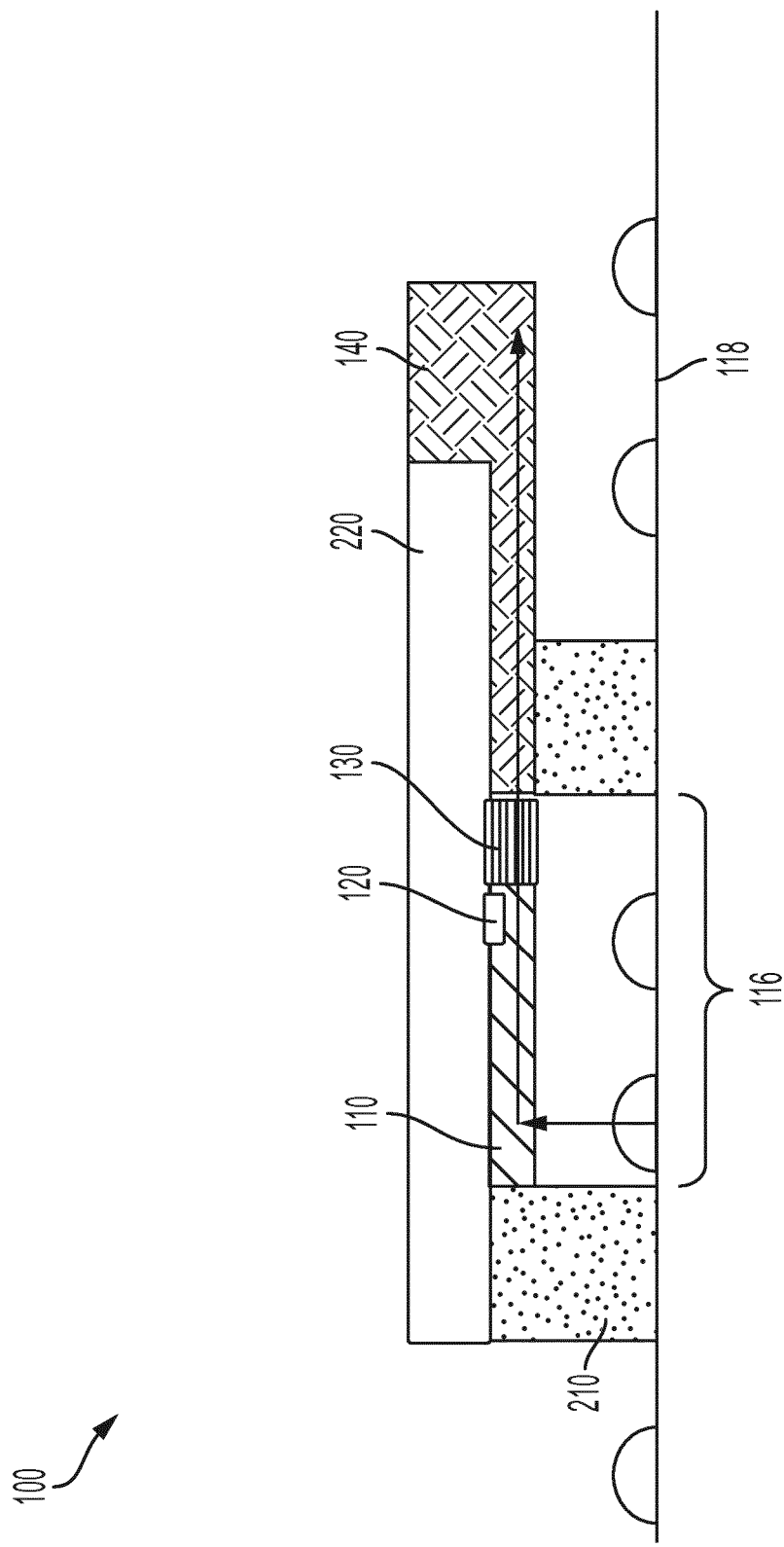
FIG. 3 is a schematic diagram showing a side view of a system for collection and analysis of a fluid from a surface, according to an illustrative embodiment.

Details regarding various embodiments of a system for collection and analysis of a fluid (e.g., a biofluid, e.g., sweat) from a surface (e.g., skin of a user) are provided herein. FIG. 1 shows a schematic diagram of system 100, according to an illustrative embodiment. FIG. 2 and FIG. 3 each show a schematic diagram of a top-down view and side view of the system, according to various embodiments. Modules 110, 120, 130, 140, 150 and 160 of FIG. 1, FIG. 2, and FIG. 3 are described below.

Collection and Delivery Module

A surface (e.g., skin) can become wet (e.g., or semi-wet) by fluid from, for example, condensation, diffusion, permeation through pores and/or ducts in a person's skin. The fluid may be a biofluid, such as sweat emerging from sweat ducts on the surface of a person's skin.

As shown in FIGS. 1-3, in certain embodiments, collection and delivery module 110 includes a surface patterned with structures 112 (e.g., collection structures) that are designed to collect fluid (e.g., a biofluid, e.g. sweat) on another wet (e.g., semi-wet) surface 118 (e.g., skin) that is in contact with (e.g., substantially in contact with) surface with the collection structures 112. Fluid is collected in a collection zone 116 of the collection surface 118 (e.g., a region of skin addressed by the surface of the device) and directed through one or more fluidic channels 114 (e.g., a fluidic channel network) towards main sensor module 120. Collection proceeds in a manner that optimizes the delay between the emergence of the fluid on the collection zone and the readout by the sensors. In certain embodiments, fluid flow is driven passively (e.g., by capillary action). In other embodiments, active flow is used (e.g., driven by one or more fluid pumps, e.g., pumps requiring power).

To efficiently deliver fluid from collection structures 112 of collection and delivery module 110 to main sensor module 120, a channel network 114 is used, in certain embodiments, and is designed to direct (e.g., funnel) fluid from collection structures 112 to a sensor in main sensor module 120. In certain embodiments, channel network 114 is designed to direct the fluid in an unidirectional flow (e.g., to improve the response time of the sensor). In certain embodiments, channel network 114 is designed to ensure that the entire surface of a sensor is in contact with the collected fluid (e.g., to improve signal performance, e.g., to improve signal strength).

Collection and delivery module 110 can be placed near collection zone 116 (e.g., in the vicinity of collection zone 116). Collection and delivery module 110 may be in contact with collection zone 116 (e.g., a specific region of skin) or it may be separated from the collection surface 118 by a spacer.

Collection zone 116 and adjacent collection structures 112 may be surrounded by a sealant material or a sealing structure 210 to ensure that most or all of the fluid cannot leak out or evaporate. For example, sealant 210 may ensure that the only possible direction of fluid transport is through collection structure 112 of collection and delivery module 110 (e.g., an O-ring may surround the perimeter of collection zone 116). Sealant 210 may include a sealant material that is semi-permeable (e.g., impermeable to a liquid of interest and permeable to air). Sealant 210 may act as a spacer layer defining a distance between collection zone 116 and collection structures 112. It may also act as a fixation system. It may include of an elastomer, gel, grease, glue (e.g., silicone or acrylate glue), an adhesive (e.g., a skin adhesive), a laminate (e.g., an adhesive trilaminate).

For fluid that emerges to a surface via pores or ducts (e.g., for a fluid such as sweat), collection structures 112 are dimensioned (e.g., sized and shaped) such that they address a plurality of pores or ducts (e.g., at least one pore or duct is addressed by the collection, e.g., a plurality of pores and ducts are addressed). For example, the density of sweat ducts on human skin is in a range from about 0.1 to about 10 ducts per mm$^2$ depending on the location on the body. In certain embodiments, collection zone 116 may have a surface area of greater than 10 mm$^2$ (e.g., to address at least one pore, e.g., at the lowest pore density of about 0.1 pore per mm$^2$). In other embodiments, the surface is larger to address greater than one pore.

For fluid in the form of drops or droplets on a surface, collection structures 112 are designed to collect fluid from the drops or droplets. Collection structure 112 typically includes at least one fluidic channel or a fluidic channel network 114.

Figure 4:
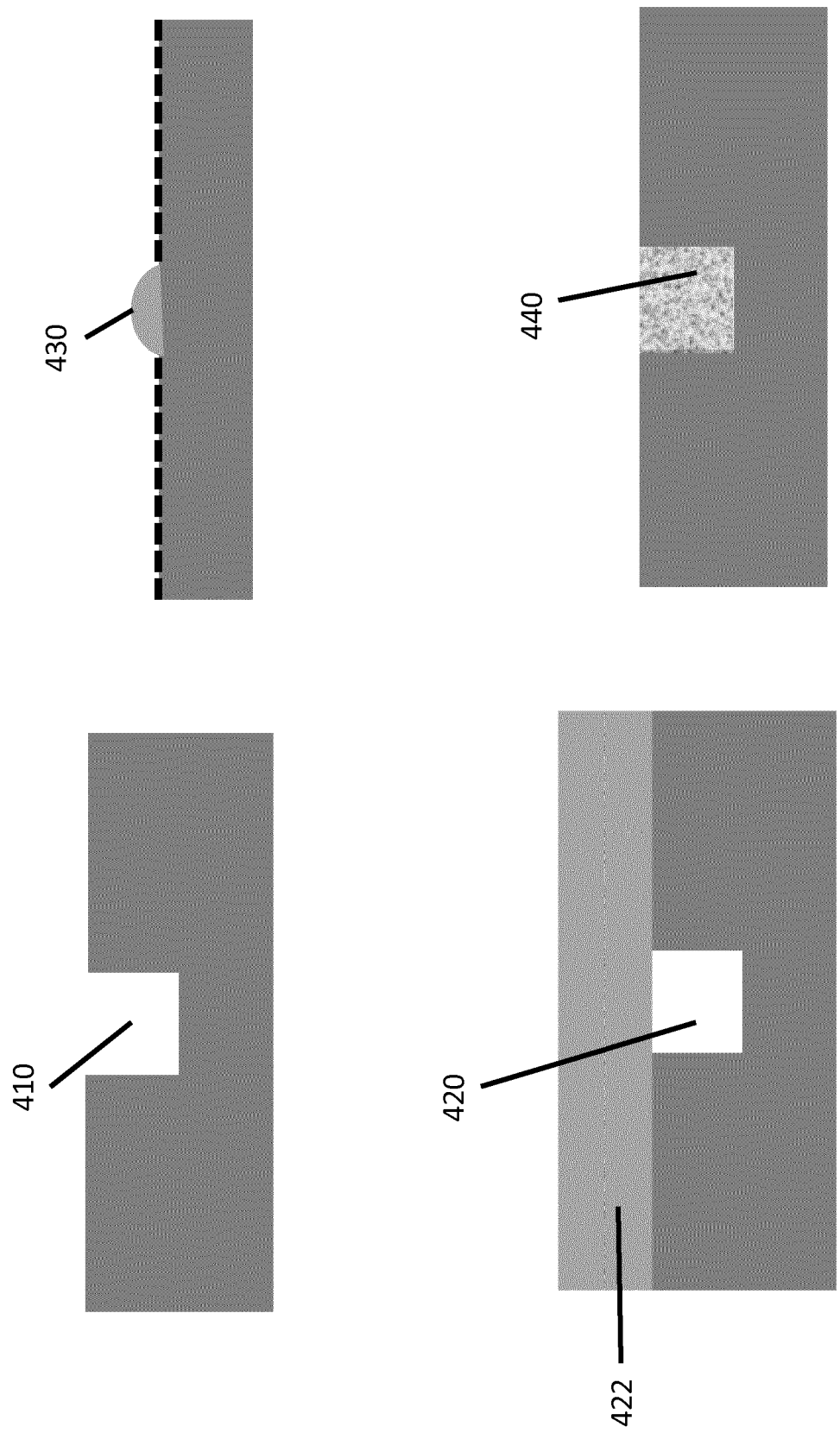
FIG. 4 is a schematic diagram showing cross sections of fluidic channels, according to illustrative embodiments.

FIG. 4 shows cross-sections of fluidic channels. As used herein, a "fluidic channel" may refer to the following implementations (or a combination thereof): an open channel such as a groove 410 in the collection zone surface, a closed microfluidic channel 420 (e.g., closed with a laminated lid 422), a "two-dimensional" ("2D") channel 430 defined by surface properties [e.g., where the channel is on a surface (e.g., does not include side walls and a top) and is defined by surface energy contrast (such as hydrophilic/hydrophilic patterning)], or a channel including a fixed gel matrix 440 that is permeable to the fluid (e.g., a groove or microfluidic channel filled with a cross-linked hydrogel that is permeable to water).

A channel comprising a gel matrix typically has a high affinity for fluid and can prevent unwanted drying of the channel (e.g., a channel filled with a hydrogel may dry slower than a channel filled with water because of the hydrophilicity of the hydrogel).

A fluidic channel (e.g., or a fluidic channel network) may be fabricated by one or a combination of the following techniques (and possibly as multilayers of one or a combination of techniques): photolithography of a photosensitive polymer such as SU-8

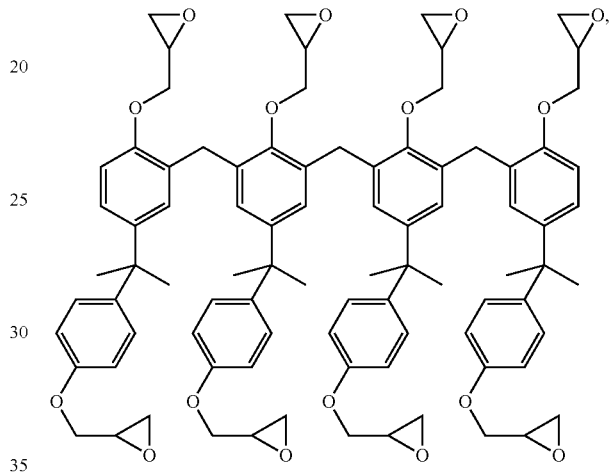

by application of a laminated plastic foil patterned by photolithography or pre-patterned (e.g., by imprinting) or pre-cut (e.g., by laser), using plastic injection, and with the grafting or deposition of a gel.

A fluidic channel (e.g., or a fluidic channel network) may include a combination of open channels (e.g., inlets where fluid is collected) and of closed channel (e.g., through which the fluid is delivered to a sensor). In some embodiments, this is achieved using a double layer of independently structured SU-8 layers bonded together. In other embodiments, this is achieved by locally covering open channels (e.g., made of a single layer of patterned SU-8) with a laminated polymer film that is affixed to the open channel layer with an adhesive (e.g., tape). The adhesive can be hydrophilic.

The surface properties (e.g., the surface energy) of the fluidic channel or channel network may be tuned by physical and/or chemical treatment(s) (e.g., to render the channel hydrophilic) to promote the wetting and filling of the channel by capillary action. This may be performed by surface activation (e.g., with oxygen plasma), by functionalization (e.g., with specific molecules), by grafting of a functional molecule to the surface (e.g., a self-assembled monolayer, e.g., of one or more silanes and/or one or more thiol(s)). A gel (e.g., hydrogel) coating can also be grafted to or coated on the surface of the fluidic channel(s).

Figure 5:
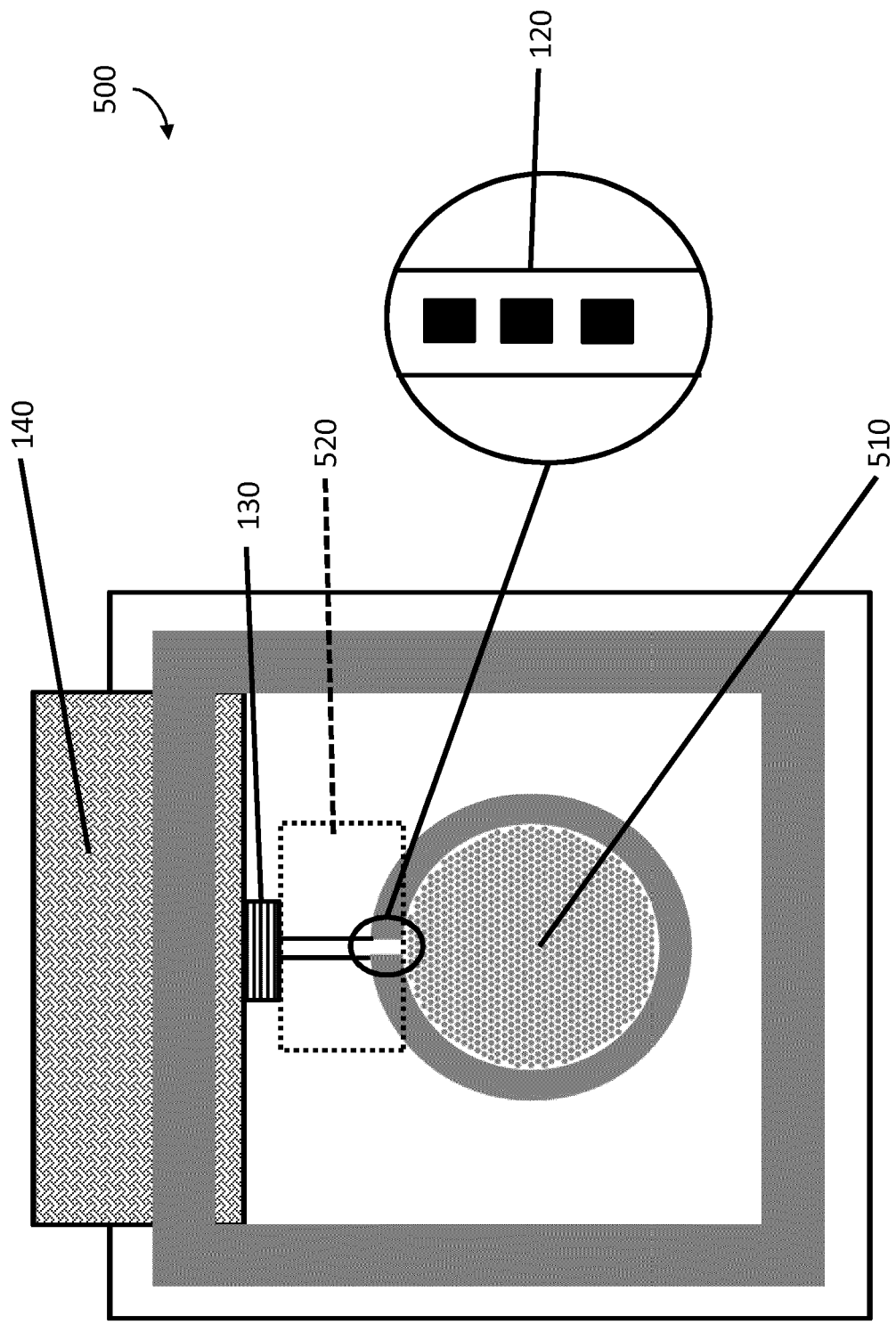
FIG. 5 is a schematic diagram showing a system for collection and analysis of a fluid from a surface with pillar-based collection structures, according to an illustrative embodiment.
Figure 6:
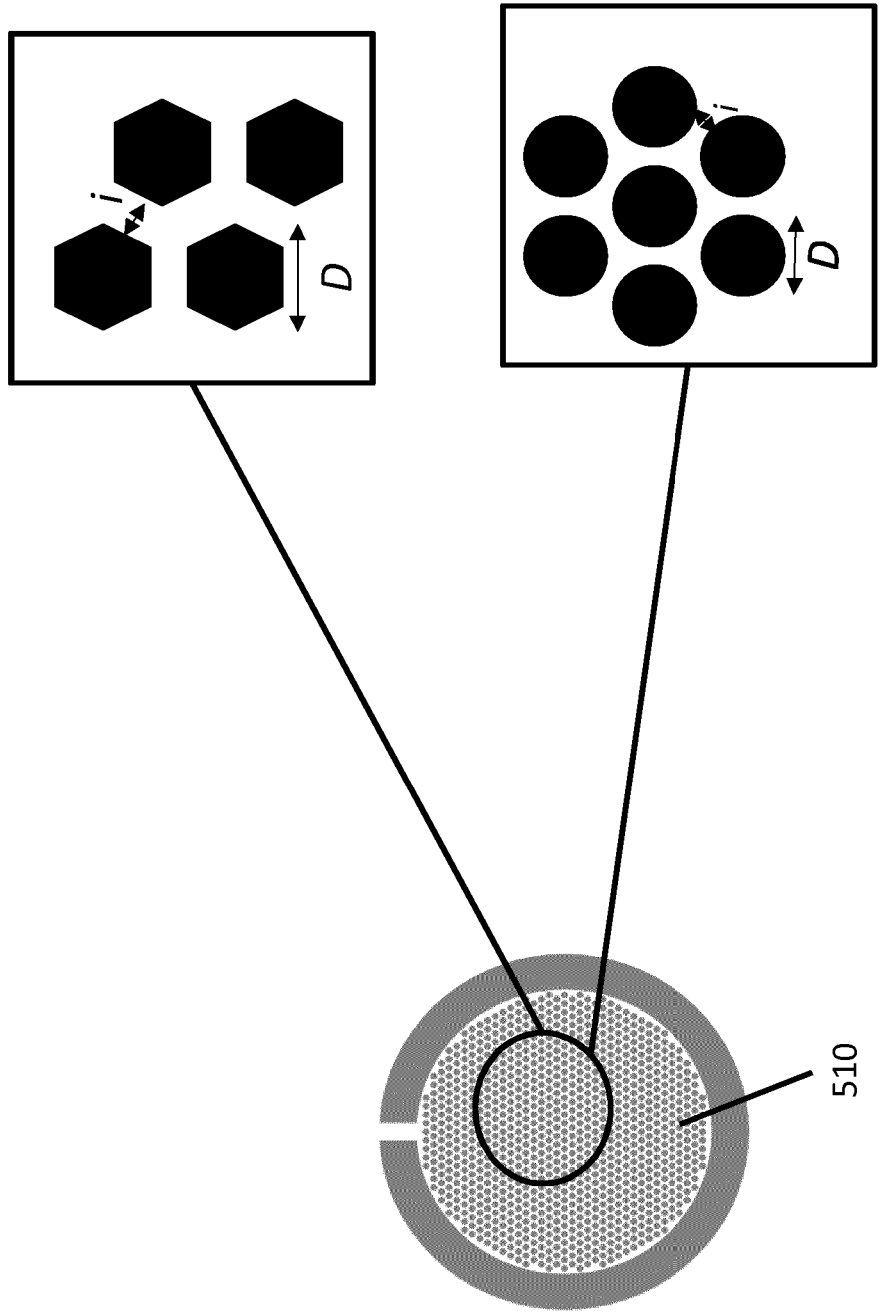
FIG. 6 is a schematic diagram showing details of pillar-based collection structures, according to an illustrative embodiment.
Figure 7:
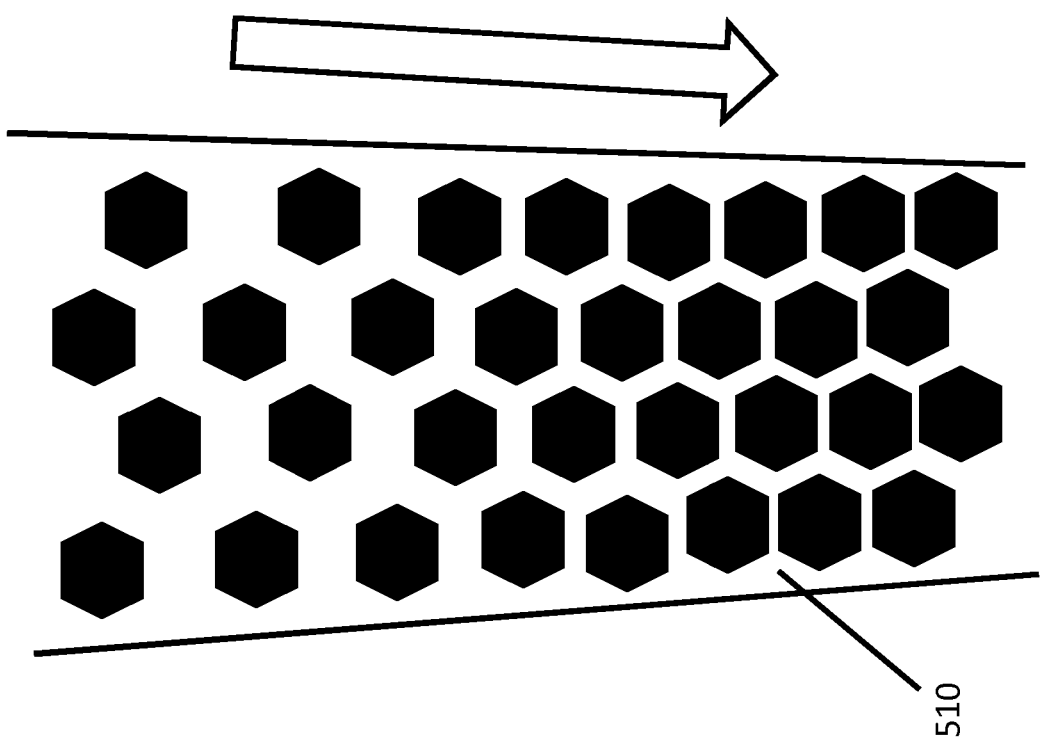
FIG. 7 is a schematic diagram showing pillar-based collection structures with an interstitial distance gradient, according to an illustrative embodiment.

A fluidic channel may include pillars or pavement structures (or arrays thereof) to reduce dead volume in the channels and to facilitate fluid transport via capillary action. FIGS. 5 and 6 show illustrative examples of a system 500 that include a microfluidic collection and delivery module 110 with pillars-based collection structures 510. In certain embodiments, collection and delivery module 110 includes an optional lid 520 locally closing the channels. The pillars (e.g., or pavement) can have two primary parameters: the pillar diameter D and the inter-pillar distance i. For sweat collection on skin, for example, the pillar diameter D and inter-pillar distance i are in a range between 1 μm to 1 mm. In certain embodiments, the pillar diameter D is in a range from about 10 μm to about 800 μm, or from about 100 μm to about 500 μm. In certain embodiments, the inter-pillar distance i is in a range from about 10 μm to about 800 μm, or from about 25 μm to about 100 μm. Each pillar array may be designed such that they have a size or interstitial distance gradient in one direction to promote directional flow towards the sensor, as shown in the illustrative example of FIG. 7.

Figure 8:
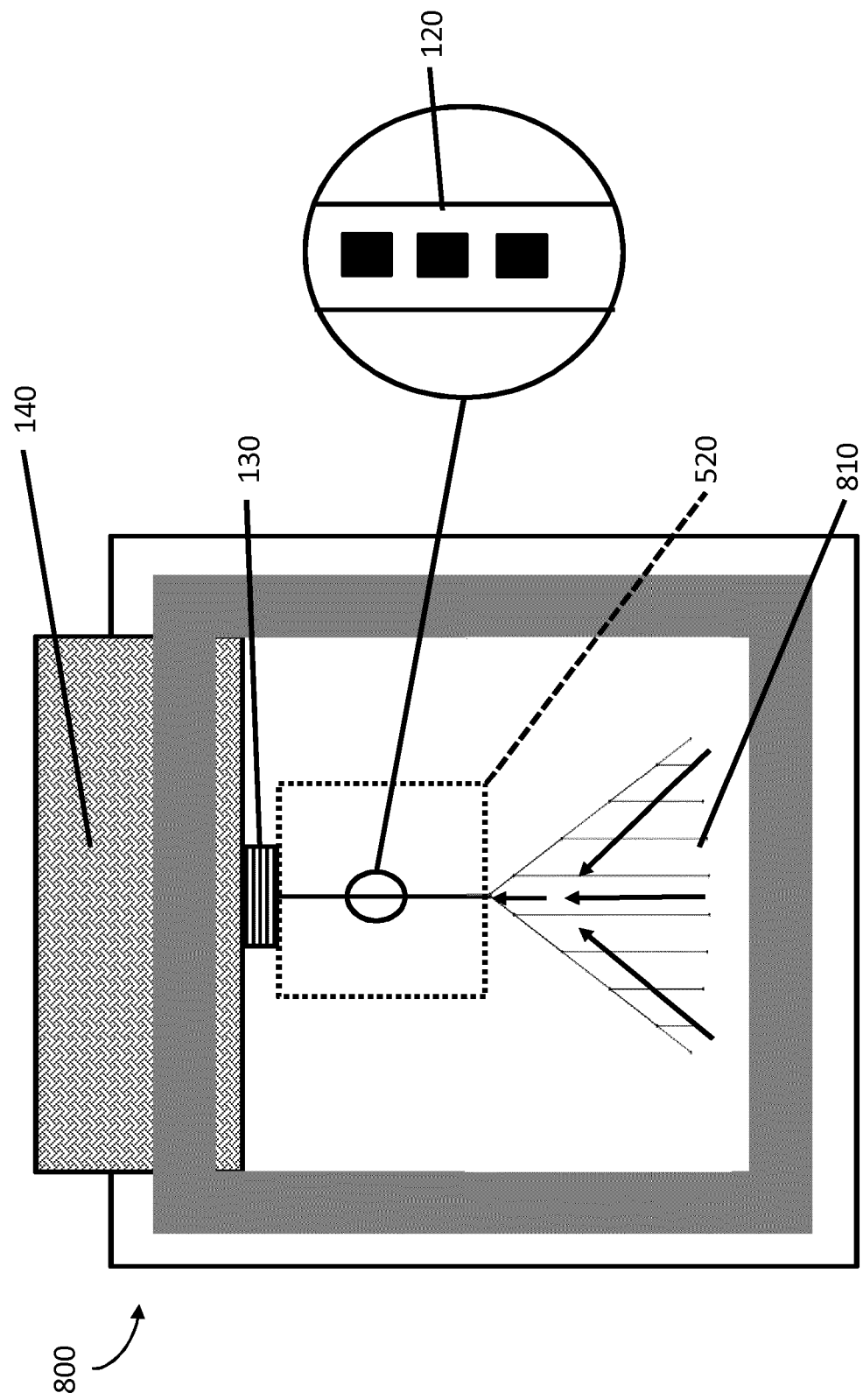
FIG. 8 is a schematic diagram depicting a system for collection and analysis of a fluid from a surface with arborescent collection structures, according to an illustrative embodiment.
Figure 9:
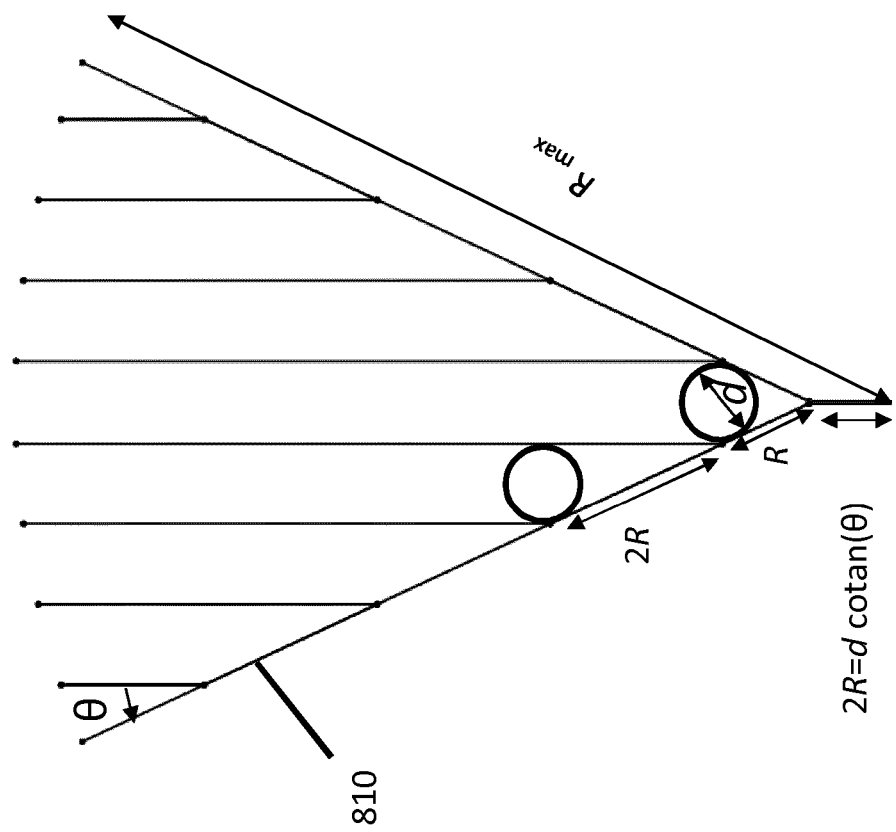
FIG. 9 is a schematic diagram showing a configuration of arborescent collection structures, according to an illustrative embodiment.

As in the system 800 shown in FIG. 8, in certain embodiments, the fluidic channel network includes arborescent collection structures and delivery channels 810 with branches that address the surface (e.g., with a regular spacing, e.g., corresponding to the spacing of pores on the skin) of collection zone 116 (e.g., the branches may have biomimetic and/or a fractal geometry). Each channel (e.g., or "branch") of arborescent collection structures and delivery channels 810 may capture (e.g., collect) fluid to be delivered to main sensor module 120, as shown in the illustrative examples of FIGS. 8 and 9. Arborescent collection structures and delivery channels 810 (e.g., or other arborescent structures) can be characterized by a "tree opening" angle ϑ, a maximum extent of the "tree" (e.g., a tree radius) $R_{max}$, and an inter-branch distance d.

The branches of the channels 810 may be designed to provide a constant opening angle to promote filling by capillary action. An example of this is shown in the illustrative example of FIG. 10. FIG. 10 shows the same structure presented in FIG. 9 but with an additional parameter: a constant opening angle (a). For example, a "2D" channel may be defined by differences in surface properties (e.g., surface energy) (e.g., using hydrophilic/hydrophilic patterning).

In certain embodiments, fluid emerges from a surface (e.g., a wet surface, e.g., skin) as droplets. For example, fluid can emerge as droplets from ducts in the surface of skin. For collecting drops (e.g., droplets) arborescent collection structures 810 (with branches separated by the inter-branch distance d) can be used. Arborescent collection structures 810 can be separated from the collection zone 116 by a spacer layer (e.g., a sealant, e.g., an adhesive) with a thickness e. In general, it is not possible to align the pores (e.g., of the skin) with the branches of arborescent collection structures 810. For example, alignment of the collection structures 810 to the pores in skin may not be practical. For example, the substrate on which the collection structures 810 are fabricated may not be transparent, preventing practical alignment of the collection structures 810 to the pores. In certain embodiments, in order to be collected, a droplet must grow until it reaches a threshold height that is determined from the spacer layer thickness e. The droplet may then need to grow laterally until the surface of the droplet reaches at least one of collection structure 810.

In certain embodiments, the maximum lateral size a droplet achieves once touching the surface of the collection zone is half the inter-branch distance d minus half the channel width w (i.e., d/2−w/2). The global dead-volume of the fluidic channel network can be increased by decreasing the inter-branch distance d and/or increasing the channel width w. In certain embodiments, the time required to transport a fluid from collection surface 118 (e.g., the surface of collection and delivery module 110) to main sensor module 120 requires a tradeoff to determine an optimum inter-branches distance d and the channel width w. The values may be selected based on a given application. For example, the spacer layer e may be designed to be as thin as possible as long as it remains functional (e.g., as a sealant, e.g., as an adhesive).

Figure 11:
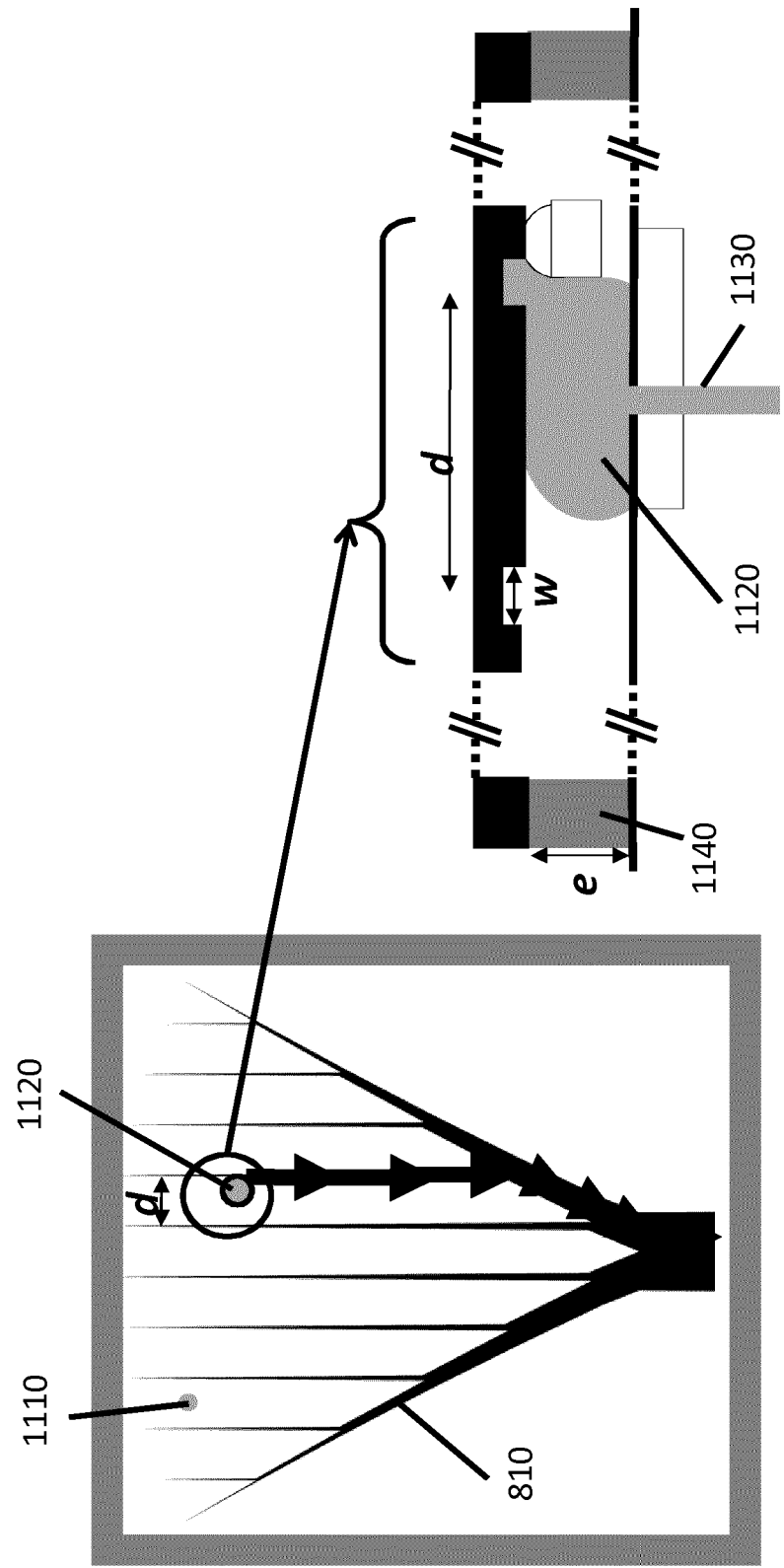
FIG. 11 is a schematic diagram representing the collection of a droplet of a fluid by an arborescent fluidic network in the presence of a spacer layer, according to an illustrative embodiment.
Figure 12:
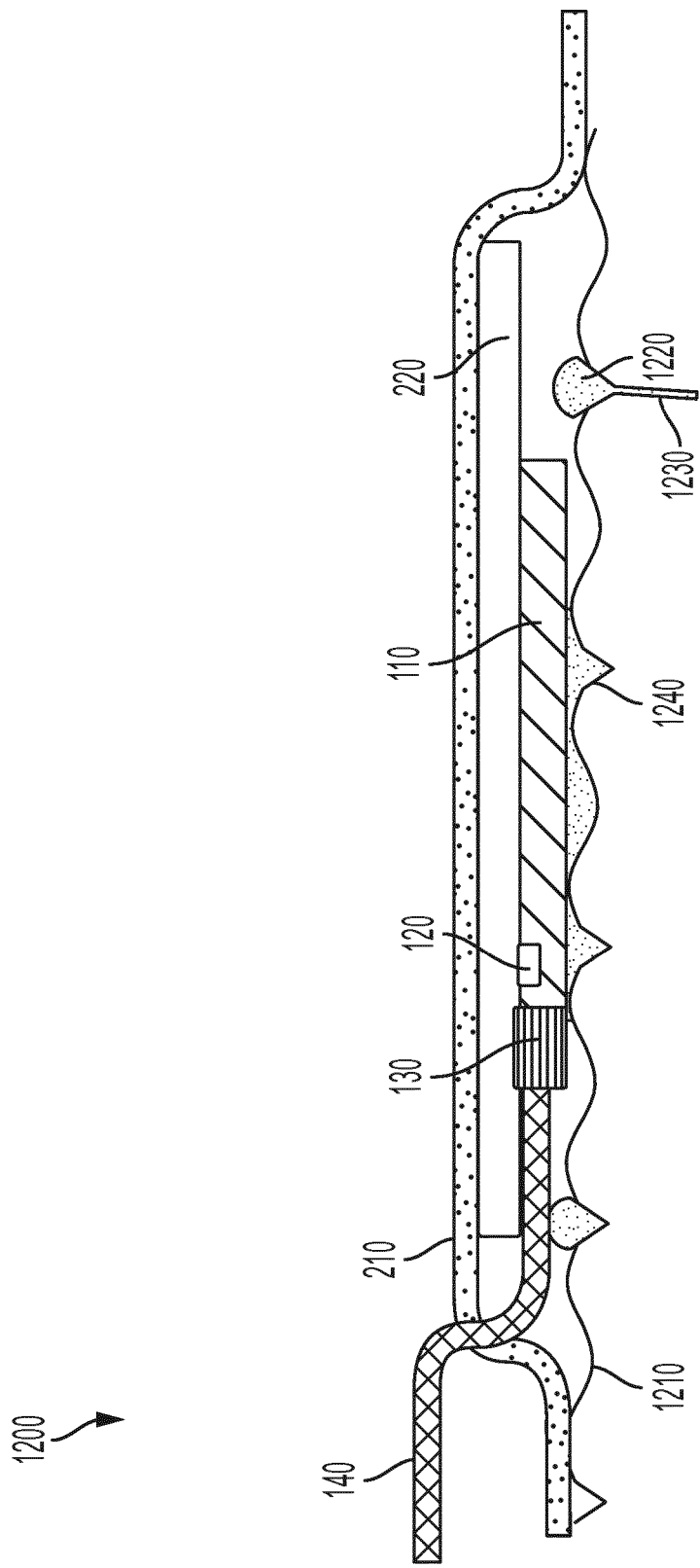
FIG. 12 is a schematic diagram representing a system for sweat collection with collection structures in direct contact with the skin and sweat transport taking place within the v-groove network of the skin, according to an illustrative embodiment.

FIG. 11 shows an illustrative example of a branch of arborescent collection structures and delivery channels 810. If the lateral dimension of a droplet 1110 is too small, it cannot reach one of collection structure 810 and will not be collected. Once the size of a droplet 1120 coming from a pore or duct 1130 reaches the lateral size (i.e., d/2−w/2), it can be collected. For fluid collection on skin, the distance d is may be in a range from about 50 μm to about 1 mm. The width of the channel may be in a range from about 1 μm to about 1 mm. When a spacer layer 1140 is present, the thickness (e) may be, for example, in a range from about 10 μm to about 500 μm. For fluid collection via collection structures on a surface that has a v-groove network (e.g., certain regions of human skin), the v-grove network itself may participate to fluid transport. This may particularly be the case in embodiments where the collection structure is applied directly to the surface (e.g., without a spacer layer, e.g., with a thin spacer layer). In this embodiment, a sealant (e.g., an adhesive, e.g. a laminate) may be applied over the edge of the collection structure (e.g., to cover both the edge of the collection structure and the surface on which the fluid is collected). FIG. 12 shows an illustrative example of a system for collection and analysis of a fluid. The system is affixed to and in direct contact with the skin 1210 by a sealant 210. A portion of sweat droplets 1220 coming from sweat ducts 1230 can spread within the v-groove network 1240 of the skin 1210 and be transported by the v-groove network 1240.

FIG. 13 is a schematic diagram showing hybrid collection structures 1300. In certain embodiments, a channel network includes both arborescent collection structures 1310 and pillar-based collection structure 1320. In certain embodiments, the arborescent structures address the surface where sweat droplets can randomly appear more efficiently (e.g., with low dead volume). In certain embodiments, pillars structures have more dead volume, however they are more robust to clogging (e.g., as fluid can find alternative path to flow if one interstice get clogged). Therefore it may be beneficial to have hybrid collection structures in which the arborescent structures (e.g., "branches") merge to the pillar-based structures (e.g., "trunk") so that in the event of clogging the trunk can still be able to carry liquid over even if some branches may be lost due to clogging.

A filter may be added to channel network 114 to exclude contaminants, depending on the application. For sweat collection, contaminants may be lipids, bacteria, particles, and/or dead skin cells. The filter may include an ensemble of obstacles that would sterically exclude (e.g., exclude based on size) the contaminants (such as an array of pillars structures, or a fiber matrix such as paper or a textile). The filter may also include a gel (e.g., a hydrogel) matrix. In certain embodiments, the pillars structures may act as a filter (e.g., if some or all of the pillar-filled fluidic channel includes a locally closed channel, e.g., the channel is closed with a lid, e.g. with a lid comprising a laminated film), for example, as depicted in the illustrative example of FIG. 13.

Collection and delivery module 110 is typically designed to optimize the delay (e.g., make the delay short, e.g., make the delay coincide with a desired frequency of measurements) between the emergence of the fluid at the collection zone and the readout by main sensor module 120. This, for example, improves the time response of the sensor. For readouts that are sensitive to diffusion (e.g., based on diffusion-limited process) (e.g., temperature and concentration measurements), this approach decreased the unwanted effects of averaging out (e.g., dilution/diffusion) of information during diffusive transport.

Collection and delivery module 110 may be designed to prevent bubbles (e.g., air bubbles) from being trapped in the system (e.g., in the fluidic channels). In order to avoid bubbles from being trapped, the fluidic channel network 114 may direct (e.g., funnel) fluid to a single channel before the fluid is delivered to main sensor module 120. Serpentine channels may intersect all the sensors serially because bubbles were found to be trapped within a branch of a Y-junction, preventing bubbles from obstructing measurements.

A serpentine structure may also be used to maximize the overlap of a fluidic channel (e.g., a microchannel) with the surface of a sensor, particularly, for example, when the sensor is wider than the fluidic channel (e.g., a disk-shaped reference electrode with a diameter greater than the width the fluidic channel).

Main Sensor Module

Chemical and/or physical analysis is performed by main sensor module 120. This analysis may, for example, include the measurement of the concentration of substances present in the fluid, the pH, the conductivity, temperature, the pressure, flow rate, the velocity of the fluid. The substances measured by the sensor may be ions (e.g., chloride, sodium, potassium), sugars (e.g., glucose), biomolecules (e.g., polynucleotides, proteins, hormones, enzymes, antigens, neuropeptides, antibodies), and any other solute.

A sensor in main sensor module 120 may be based on a physical and/or chemical principle. For example, a sensor may use an electrochemical, electrical, or optical signal. a sensor may be based on an electrode, based on a semiconducting element (e.g., a capacitor e.g., a MOSCAP) or a transistor.

The measurement of pH or of the concentration of a substance may be based on a field-effect transistor (e.g., an ion-sensitive field-effect transistor, (ISFET)) or the electrochemical response of an electrode (e.g., the measurement of an open-circuit potential, a voltammetric measurement, an amperometric measurement, or an impedance measurement). The surface a sensor may be functionalized to detect a specific substance.

In certain embodiments, the sensors in main sensor module 120 may include one or more arrays of field effect transistors (FETs) (e.g., ion sensitive FETS (ISFETs), e.g., fully depleted FETs (FD-FETs)). The array(s) of FETs may include FETs with a ribbon architecture fabricated on a fully depleted silicon-on-insulator substrate with a buried oxide layer (an FD-SOI substrate). The present disclosure encompasses the recognition that the dimensions and design of the FD-SOI substrate allows for devices with less complex fabrication processes, improved electrostatic control of the FET, a decreased parasitic capacitance between source and drain, decreased leakage currents, and decreased power consumption compared to previous technology.

The FD-SOI substrate allows FD-FETs to be fabricated with a ribbon-like structure with less strict dimensional constraints. Thus, FD-FET sensors can be fabricated with a larger sensing surface area (e.g., for improved sensor signal) than was possible using previous approaches, while maintaining the excellent electrical properties of the FD-FET. For example, the surface area of the gate of the semiconductor sensor (e.g., an FD-FET sensor) can be in a range from about 1 $\mu m^2$ to about 1000 $\mu m^2$ or larger. In certain embodiments, the surface area of the gate of the semiconductor sensor (e.g., an FD-FET sensor) is in a range from about 35 $\mu m^2$ to about 150 $\mu m^2$.

In certain embodiments, the FET sensors have liquid gates that are functionalized for the detection of selected biomarkers. For example, one or more of the sensors may have a gate that includes hafnium dioxide ($HfO_2$) (e.g., for use as a pH sensor). Each sensor (e.g., the gate of each FET) is functionalized to detect and/or quantify a biomarker of interest.

Examples of sensors which may be used in the systems, methods, devices, apparatus, and architectures presented herein are described in European Patent Application No. 16188227.9 filed Sep. 10, 2016, U.S. patent application Ser. No. 15/453,920 filed Mar. 9, 2017, International Patent Application No. PCT/IB2017/055456 filed Sep. 11, 2017, and U.S. patent application Ser. No. 15/913,714 filed Mar. 6, 2018, International Patent Application No. PCT/EP2018/077793 filed Oct. 11, 2018, the contents of which are incorporated herein in their entirety.

Main sensor module 120 can also include sensors for measuring other properties or the environment. For example, main sensor module 120 may include a temperature sensor, a flow rate sensor, a conductivity sensor, an ionic strength sensor, a pressure sensor, and/or a pH sensor.

A conductivity or ionic strength sensor may be based on the impedance readout of a pair of electrodes (e.g., platinum electrodes or Ag/AgCl electrodes).

The temperature sensor may be based on a thermocouple, thermistor, a diode-based temperature sensor or a resistance temperature detector (RTD).

The pressure sensor may be a gauge-based pressure sensor, a MEMS based pressure sensor, a piezoresistive pressure sensor.

A flow rate sensor may sense the flow rate and/or the velocity of the fluid based on heat transfer detection (e.g., a calorimetric flow meter, hot wire flow meter, time-of-flight flow meter). A capacitive flow sensor may be used to measure flow rate based on the change of impedance of an electrode. An electrokinetic flow rate sensor may be used to measure flow measurement using measurements of streaming potential. An acoustic or optical flow meter may be used to measure flow rate based on the Doppler effect. A flow meter may also measure flow rate based on differential pressure measurements.

Main sensor module 120 may also include a reference device, such as a non-functionalized instance of a sensor to allow for differential measurements.

Main sensor module 120 may also include a reference electrode producing a stable reference voltage (such as a silver-silver chloride electrode).

The sensors of main sensor module 120 may be functionalized to sense a specific molecule. The functionalization may be based on at least one of the following techniques: the deposition of a thin film on the surface of the sensor, a functional molecule grafted to the surface of the sensor, and/or a functional membrane acting as a selective barrier for the molecule to be sensed. Functional thin films of interest may be dielectrics and/or metal, for instance hafnia, silver chloride, and iridium oxide. A functional molecule grafted on the sensor may be for instance a self-assembled monolayer. A functional membrane may be for instance an ion selective membrane or a functionalized polymer matrix.

A polymer layer or gel (e.g., hydrogel) layer may be deposited or grafted on top of a sensor for at least one of the following purposes: to prevent unwanted drying of the sensor (e.g., a hydrogel has a high affinity for water), to physically protect the sensor (e.g., protection from damage by contact or from electrostatic discharge), to filter out a contaminant (e.g., for sweat collection, lipids, bacteria, particles, and/or dead skin cells may be filtered out), to facilitate sensing via a high affinity for a substance of interest that is being sensed (e.g., a substance of interest may have a higher partition coefficient in a gel relative to in the fluid) and/or to act as a selective barrier that may exclude some substances (e.g., such substance has a lower partition coefficient in the gel relative to the fluid) that may interfere with the functioning of the sensor (e.g., impacting the cross-sensitivity to the substance being sensed). For example, negatively charged species may be enriched and positively charged species may be depleted within a positively charged hydrogel. These properties may be used to improve sensing of a specific charged substance.

Figure 14:
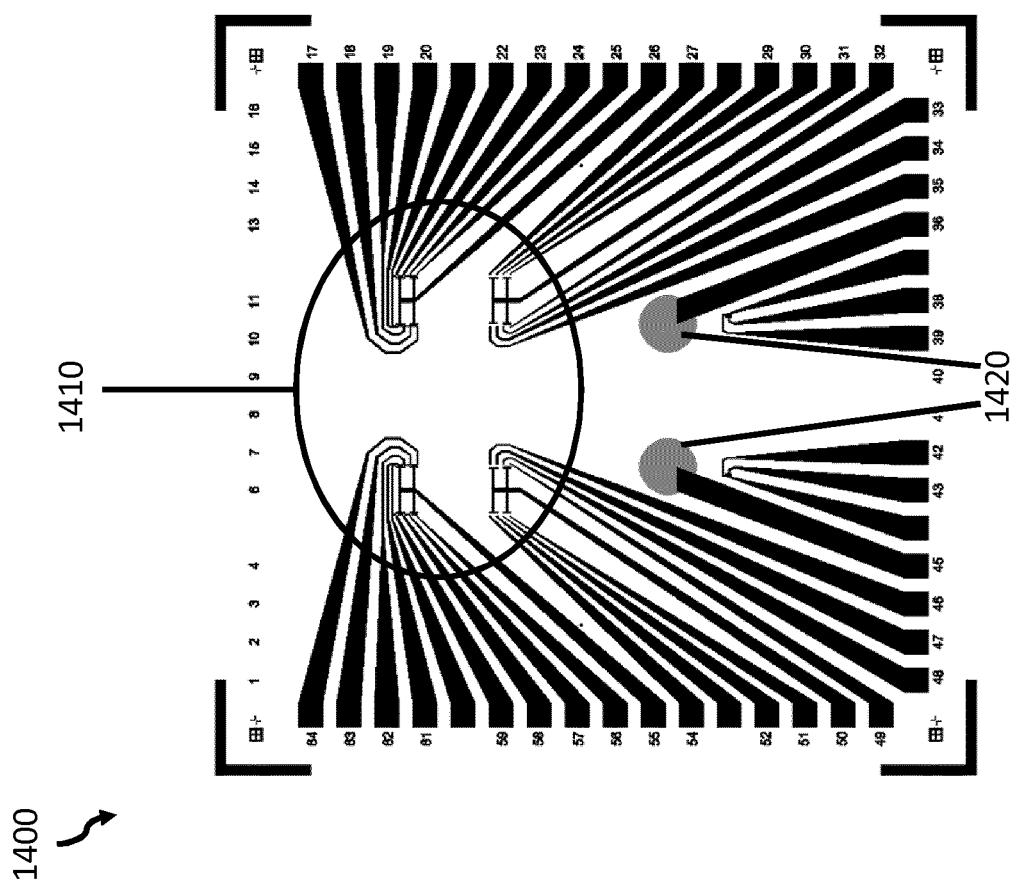
FIG. 14 is an illustration of a main sensor module, according to an illustrative embodiment.

FIG. 14 shows an illustrative example of main sensor module 1400 that includes 32 ISFET sensors 1410 and 2 reference electrodes 1420.

Flow Regulation Module

Flow regulation module 130, shown in FIGS. 1-3, controls the fluid flow in order to optimize the operation and response time of main sensor module 120. Flow regulation module 130 is designed to optimize the delay time between the emergence of the fluid on the collection zone and the readout by the sensors, while preventing the drying out of the collection and delivery system and/or the sensors surface. Flow regulation module 130 may be passive or active (e.g., actuated by a powered pump, e.g., controlled by an electronic device connected to the system).

Flow regulation module 130 comprises at least one of the following components: a capillary pump [e.g., comprising an array of pillars or pavements and/or a wicking or absorbent material (e.g., a paper or a textile)], a patterned surface [e.g., with a particular surface property (e.g., surface energy)], a barrier (e.g., a hydrophobic zone for flow of a water-based solution), and/or a fluidic valve.

Figure 15:
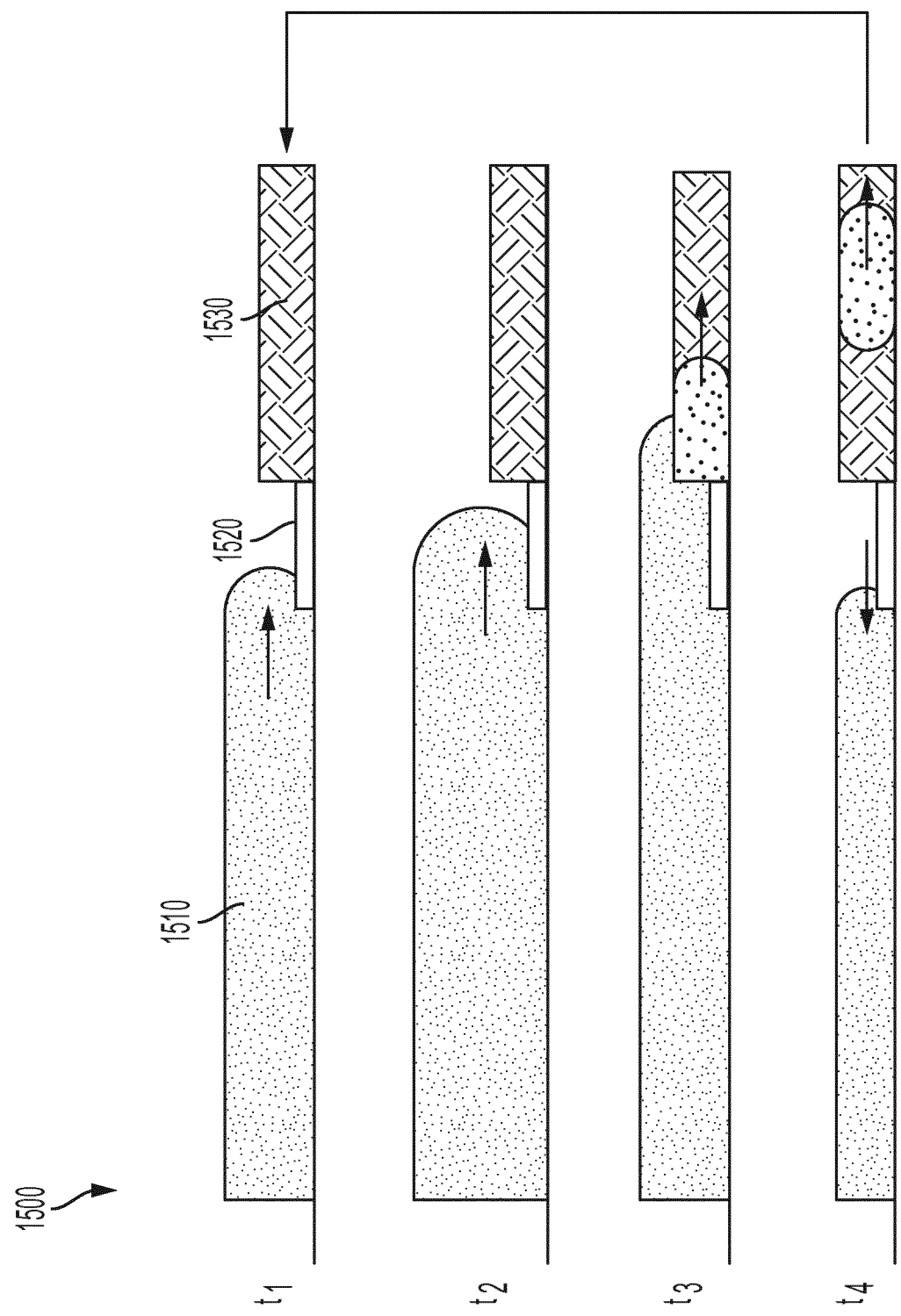
FIG. 15 is a schematic diagram depicting a flow regulation process with a flow regulation module, according to an illustrative embodiment.
Figure 16:
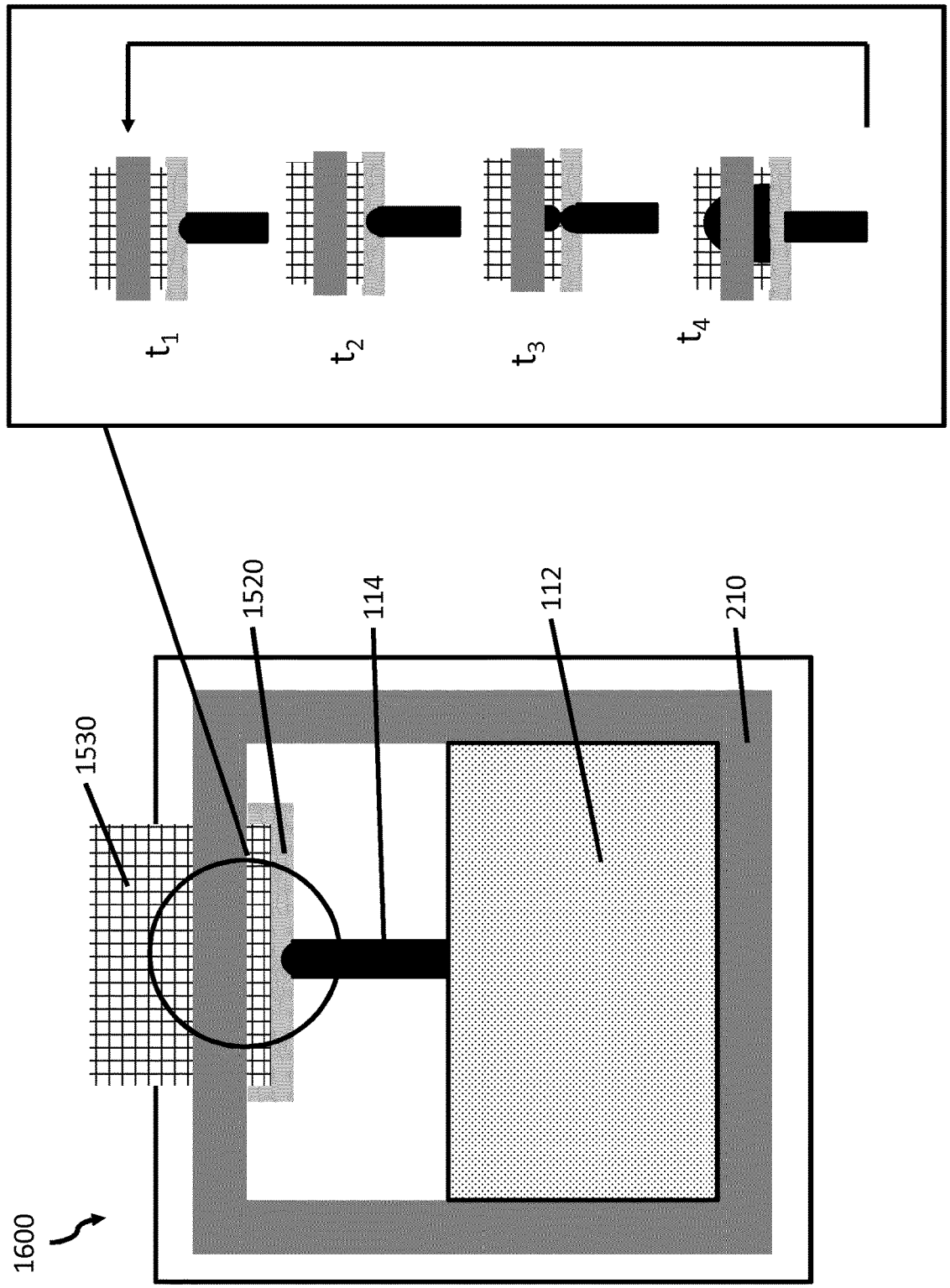
FIG. 16 is a schematic diagram showing a top view of a system for collection and analysis of a fluid from a surface with a flow regulation module, according to an illustrative embodiment.

Flow regulation module 130 may be a passive flow regulation module. A passive flow regulation module may be an overflow control device based on the combination of a surface patterned with a give surface property (e.g., surface energy) (e.g., that provides a flow barrier) and a high flow rate (e.g., high absorption rate) capillary pump. An overflow control device is dimensioned (e.g., shaped and sized) such that the surface property (e.g., surface energy) barrier always guarantees that collection and delivery module 110 and main sensor module 120 remain wet even at a low or zero flow rate of fluid from the collection zone (after initial wetting). Meanwhile, the capillary pump is dimensioned (e.g., shaped and sized) to absorb the fluid emerging in the collection zone even at maximum flow rate. FIGS. 15 and 16 show illustrative examples of such an overflow device.

FIG. 15 is a schematic diagram showing a flow regulation process 1500 by flow regulation module with a passive overflow device. In certain embodiment, flow regulation module includes a surface property barrier 1520 and a wicking material or capillary pump 1530. At $t_1$, a fluid 1510 flowing from main sensor module or collection and delivery module reaches a surface property barrier 1520 (e.g., a hydrophobic barrier). At $t_2$, as the volume of the fluid 1510 grows, the fluid passes surface property barrier 1520 and approaches a wicking material or capillary pump 1530. At $t_3$, when the fluid 1510 reaches the wicking material or capillary pump 1530, part of the fluid is absorbed by the wicking material 1530, or transported by the capillary pump. At $t_4$, the fluid 1510 breaks into two parts, with one part transported by the wicking material or capillary pump 1530 and the other part flowing back.

FIG. 16 is a schematic diagram showing a top view of a system 1600 for collection and analysis of a fluid from a surface with a flow regulation module, according to an illustrative embodiment.

An active flow regulation module may be based on an actuated fluidic valve such as a mechanical valve, a pneumatic valve, a hydraulic valve or an electrovalve (e.g., based on the control of the electrowetting of an interface or based on the control of electroosmotic flow).

In certain embodiments, flow regulation module 130 is positioned (e.g., implemented) between main sensor module 120 and waste module 140. In other embodiments, flow regulation module 130 is positioned between collection and delivery module 110 and main sensor module 120, or embedded within main sensor module 120.

Waste Module

Waste module 140 is designed to collect and/or dispose of the fluid after analysis. It may be based on a capillary pump, for instance an array of pillars (e.g. hexagonal) or pavements and/or of a wicking material based for instance on paper, textile, gel or an absorbent material. This pump or wicking material may be in turn connected to an absorbent pad acting as a waste reservoir. The reservoir may be dimensioned (e.g., sized and shaped) so that it is never full (e.g., the rate of evaporation is equal to or greater than the rate of waste collection). Thus, in certain embodiments, fluid collection can proceed continuously (e.g., over long period of time without interruption). Waste module 140 may be designed in such way as to have one end promoting fluid evaporation.

Waste module 140 may include a wicking material that is mounted at the outlet of any of the modules described herein (e.g., such that all exiting fluid is collected by the wicking material). In certain embodiments, the wicking material may be installed on the same plane as any of the modules described herein. For example, the wicking material may be separated from the surface of the collection zone by the sealant material.

Wetting Sensor Module

Wetting sensor module 150 may indicate if some or all of the above-mentioned modules are wet and provide an estimate of the flow rate during the filling of the system. It may, for example, include a series of electrodes installed in some or all of the modules including 110, 120, 130 and 140 (and possibly more than one per module). By performing conductivity measurements between pairs of electrodes, it is possible to measure whether there is ionic contact between them and hence whether the path between them is wet. By using various combinations of electrodes, it is thus possible to track the fluid progression along the way, and hence to compute an estimate of the flow rate using the known geometry and the fluidic capacity of the system.

Some of the electrodes of wetting sensor module 150 may be installed face-to-face as pairs. The electrodes may comprise a noble metal and be actuated in alternating current (AC) (e.g., in the 1 to 100 kHz range). The electrodes may be also actuated in direct current (DC) [e.g., where a voltage is applied with reference to (e.g., versus) a silver/silver chloride (Ag/AgCl) electrode(s)].

Figure 17:
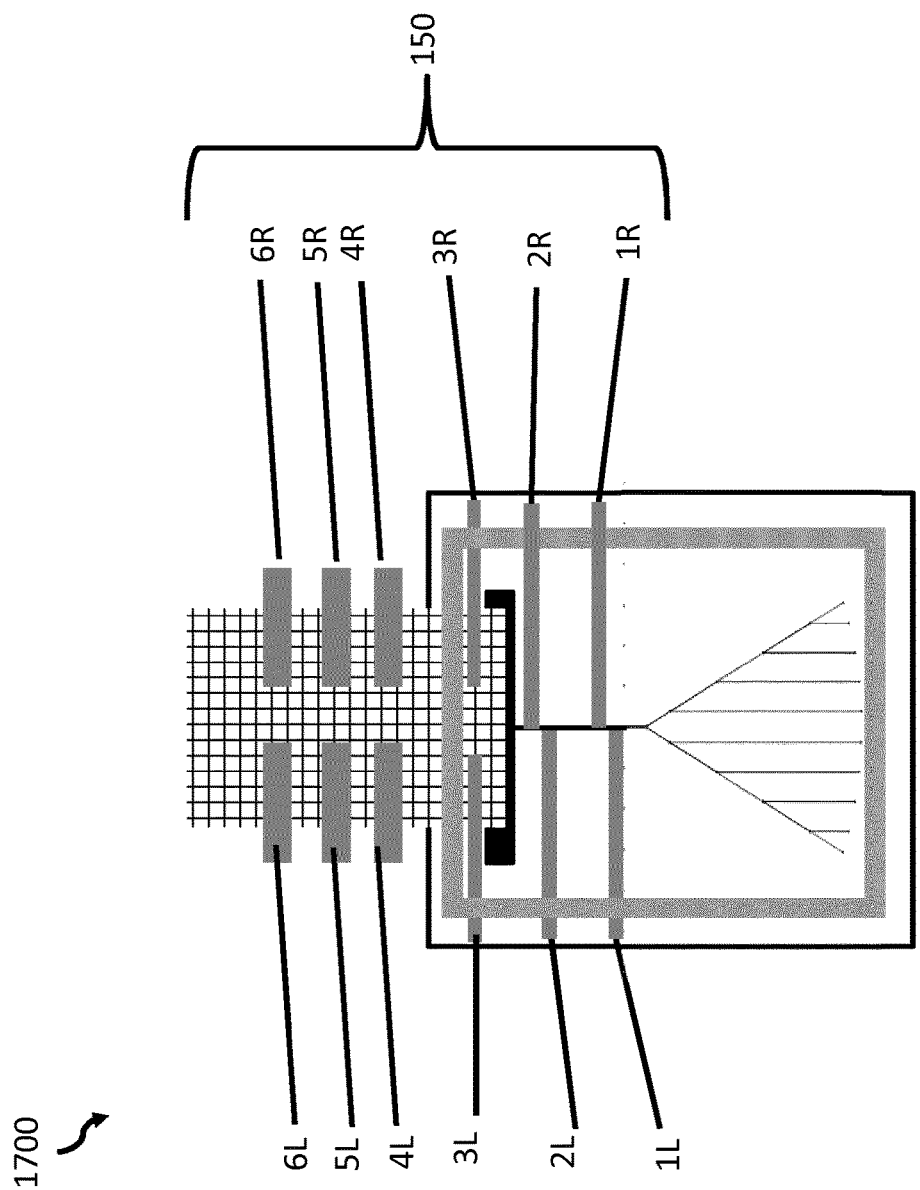
FIG. 17 is a schematic diagram of a wetting sensor module, according to an illustrative embodiment.

FIG. 17 shows an illustrative example of a system 1700 equipped with wetting sensor module 150. In certain embodiments, wetting sensor module 150 includes six pairs of electrodes (1L-1R, 2L-2R, 3L-3R, 4L-4R, 5L-5R and 6L-6R) located in modules 110, 120, 130 and 140. As shown in FIG. 17, electrodes 1L and 1R are disposed in collection and delivery module 110. Electrodes 2L and 2R are disposed in main sensor module 120. Electrodes 3L and 3R are disposed in flow regulation module 130. Electrodes 4L, 4R, 5L, 5R, 6L and 6R are located in waste module 140.

Chemical Sensor Activation Module

The system may include a chemical sensor activation module 160 to chemically activate the sensor once (e.g., during fabrication), repeatedly (e.g., in order to reactivate the sensor during use) and/or on demand (for instance by actuation by a connected electronic device).

Chemical sensor activation module 160 may include all or some of the following component (possibly more than one instance of each): a fluidic inlet for the loading of the chemical solution, a fluidic reservoir to store it, a dedicated delivery fluidic channel or fluidic channel network (as described previously), and/or a dedicated flow regulation module (as described previously). It may be formed by a set of independent lines dedicated to a specific chemical or purpose (each line including for instance of inlet, reservoir, channel and flow regulation module).

The fluidic reservoir may include a cavity in which the chemical solution is loaded through the inlet once (e.g., at the time of fabrication) or repeatedly (e.g., by an electronic device connected to the system with fluidic connection, e.g., a user of the device). The fluidic reservoir may include an enlarged version of a fluidic channel (e.g., as described earlier) dimensioned (e.g., shaped and sized) in a way to store the required quantity of the chemical. For example, may be a closed fluidic channel that encloses (e.g., encapsulates) the collected fluid and prevent evaporations (e.g., as described earlier).

The chemical solution may contain at least one substance useful for the operation of at least one of the sensors of main sensor module 120. The chemical solution may be a solution providing necessary conditions for a sensor to perform well (or a buffer solution, e.g., a pH buffer), a substance used to functionalize a sensor, a substance used to reactivate or renew the functionalization of a sensor, a substance that reacts or forms a complex with the substance to be sensed, and/or a flushing or cleaning solution.

The dedicated flow regulation module(s) of chemical sensor activation module 160 may perform passively or actively (as described previously).

The dedicated delivery fluidic channel or channel network for chemical activation may intersect with the main delivery channel or channel network of the collection and delivery module. In certain embodiments, a reaction chamber is incorporated at the intersection of these modules.

Figure 18:
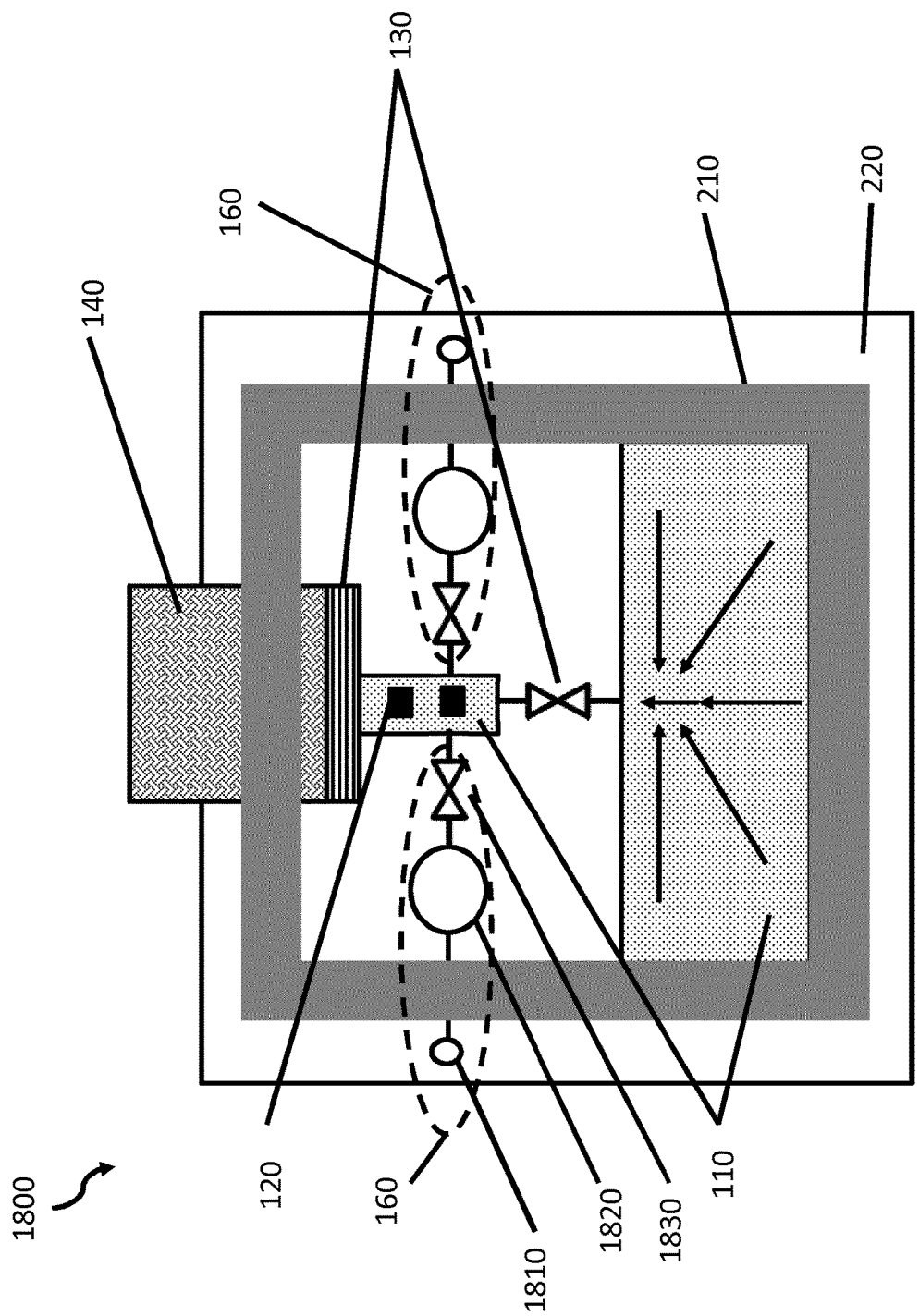
FIG. 18 is a schematic diagram of a chemical sensor activation module, according to an illustrative embodiment.

FIG. 18 shows an illustrative example of a system 1800 equipped with a chemical sensor activation module 160 with two lines and flow regulation based on a fluidic valve. Each line includes a separate set of inlet 1810, reservoir 1820, channel and fluidic valves 1830 and can be dedicated to a specific chemical or purpose.

Integration within a Microchip or Microchip Assembly

Some or part of the system (e.g., a portion (up to all) of the modules) described above may be integrated on a microchip or a microchip assembly. The microchip may further include a device to perform computation with memory to store calibration data. FIGS. 19 to 22 show illustrative examples of systems on a microchip.

Figure 19:
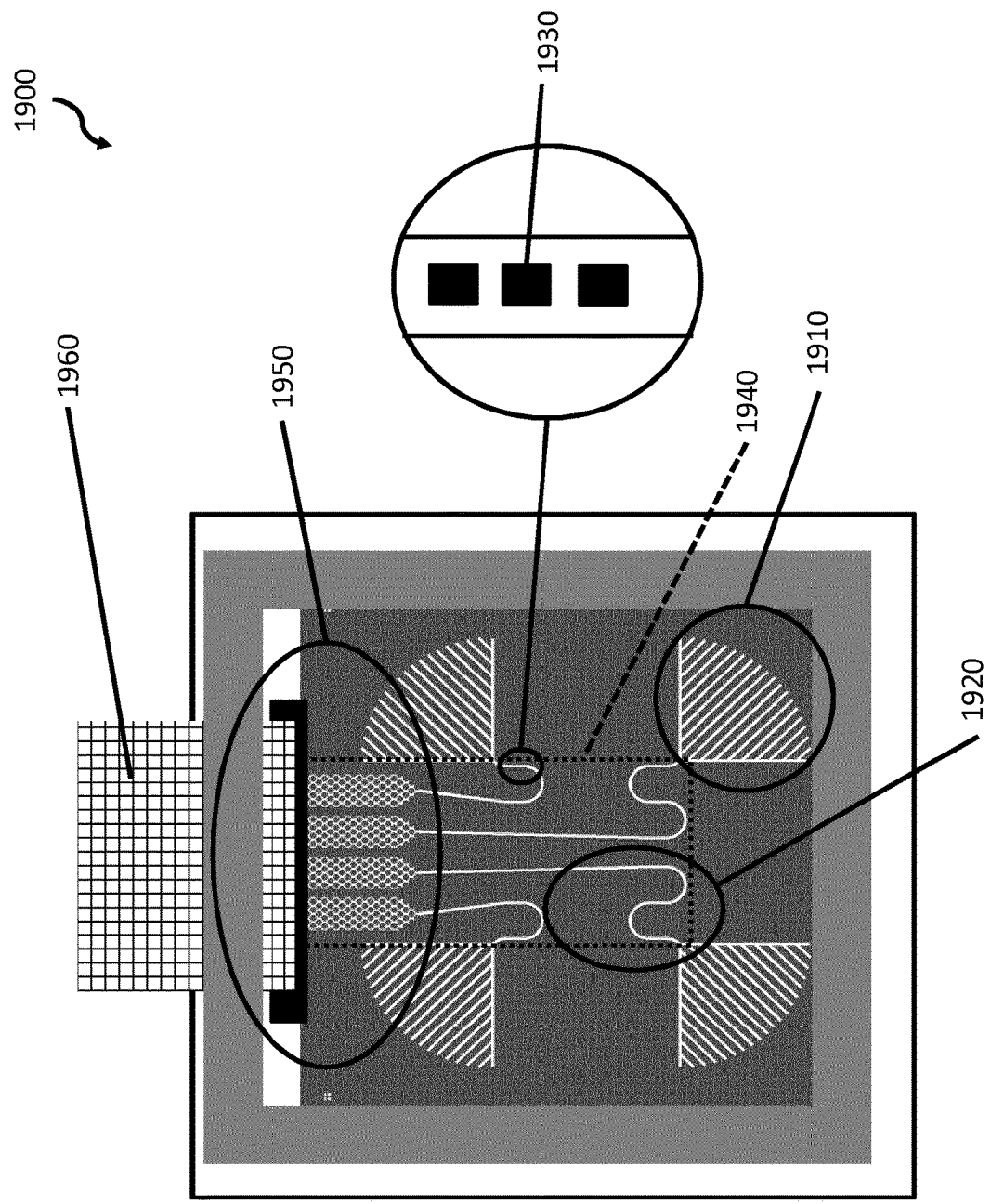
FIG. 19 is a schematic diagram of a system for collection and analysis of a fluid from a surface, according to an illustrative embodiment.

FIG. 19 shows an illustrative example of a system 1900 that can be integrated on a microchip. System 1900 includes a collection and delivery module with four groups of arborescent collection structures 1910 located at four corners of the collection zone. The collection and delivery module can include microfluidic delivery channels 1920 which are disposed on top of or in the vicinity of sensors 1930, so that the fluid (e.g., sweat) collected can be transported to sensors 1930. An optional lid 1940 can locally close the channels if needed. System 1900 can also include a flow regulation module 1950 with a capillary pump and a hydrophobic barrier. A waste module 1960 with a wicking strip and an absorbent pad can be used to collect and dispose of the fluid. The hydrophobic barrier can be disposed between the channel outlet and the wicking strip.

Figure 20:
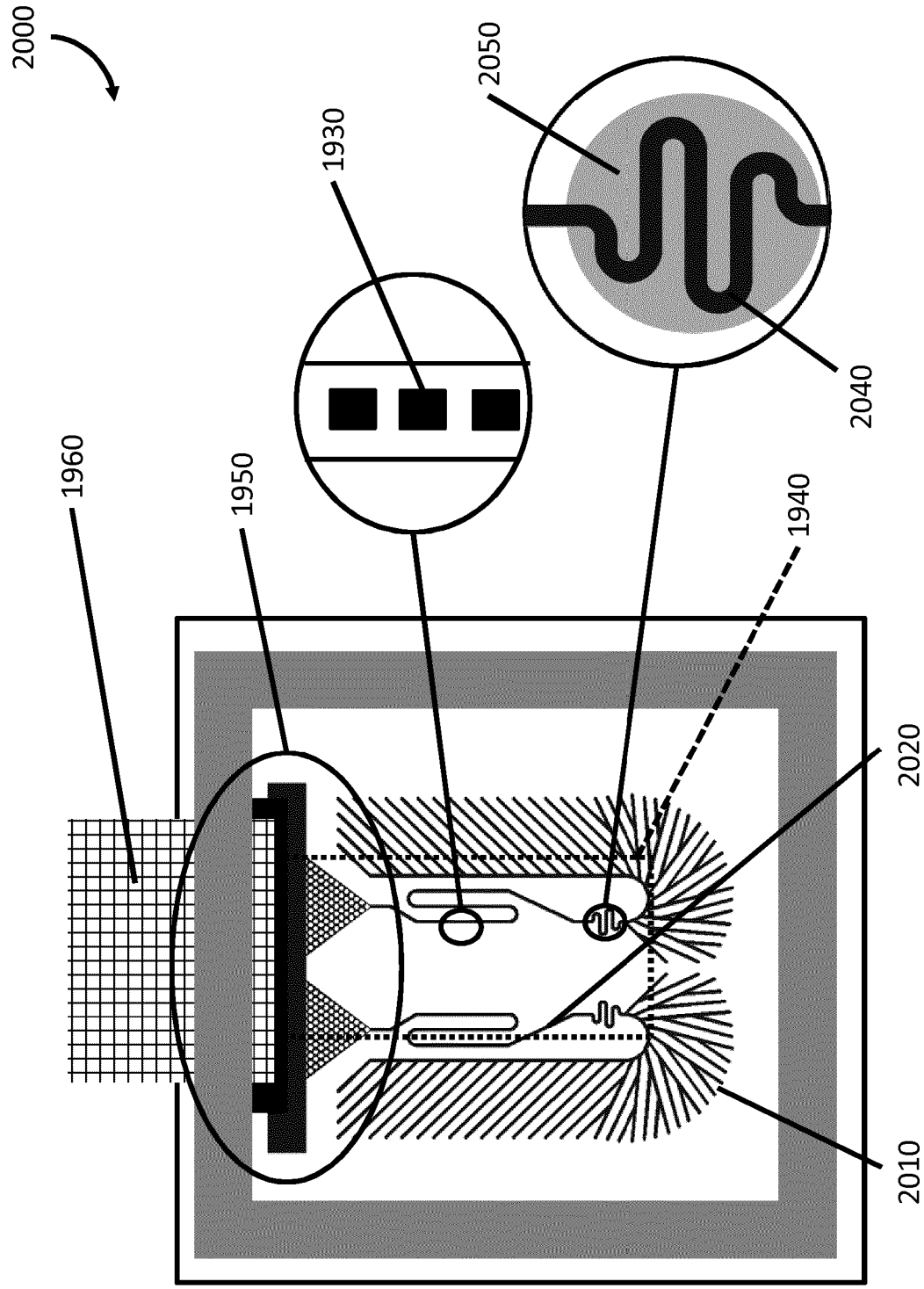
FIG. 20 is a schematic diagram of a system for collection and analysis of a fluid from a surface, according to an illustrative embodiment.

FIG. 20 shows another illustrative example of a system 2000 that can be integrated on a microchip. System 2000 includes two groups of arborescent collection structures 2010 to collect a fluid (e.g., sweat), and microfluidic delivery channels 2020 to transport the fluid to the sensor 1930. In certain embodiments, system 2000 includes serpentine structure 2040 to maximizing the overlap area of microfluidic delivery channel 2020 over a disk-shaped reference electrode 2050. An optional lid 1940 can locally close the channels if needed. System 2000 can also include a flow regulation module 1950 with a capillary pump and a hydrophobic barrier. A waste module 1960 with a wicking strip and an absorbent pad can be used to collect and dispose of the fluid.

Figure 21:
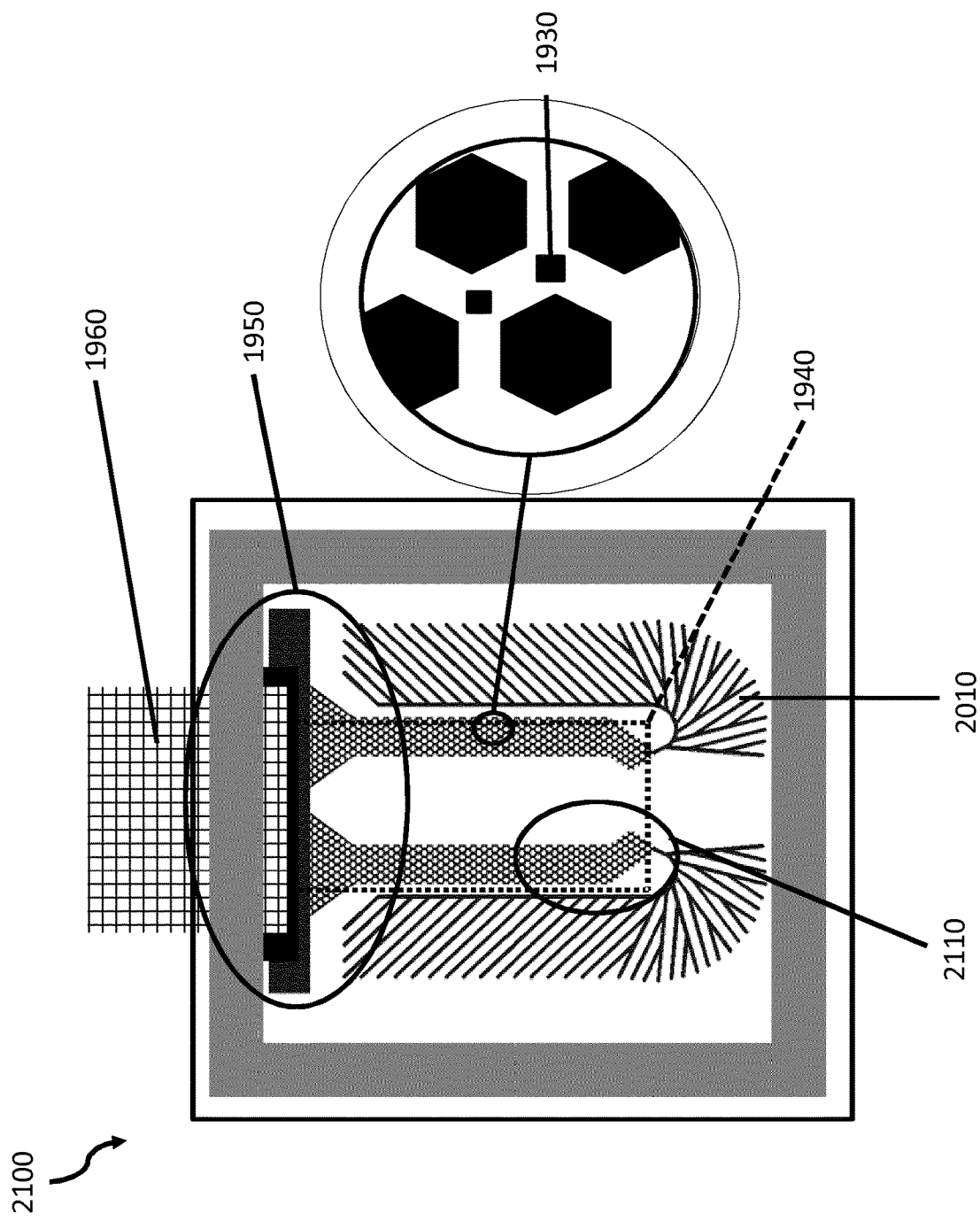
FIG. 21 is a schematic diagram of a system for collection and analysis of a fluid from a surface, according to an illustrative embodiment.

FIG. 21 shows another illustrative example of a system 2100 that can be integrated on a microchip. System 2100 includes two groups of arborescent collection structures 2010 to collect a fluid (e.g., sweat). System 2100 includes pillar-based delivery channels 2110 which transport the collected fluid (e.g., sweat) to the sensors 1930. An optional lid 1940 can locally close the channels if needed. System 2100 can also include a flow regulation module 1950 with a capillary pump and a hydrophobic barrier. A waste module 1960 with a wicking strip and an absorbent pad can be used to collect and dispose of the fluid.

Figure 22:
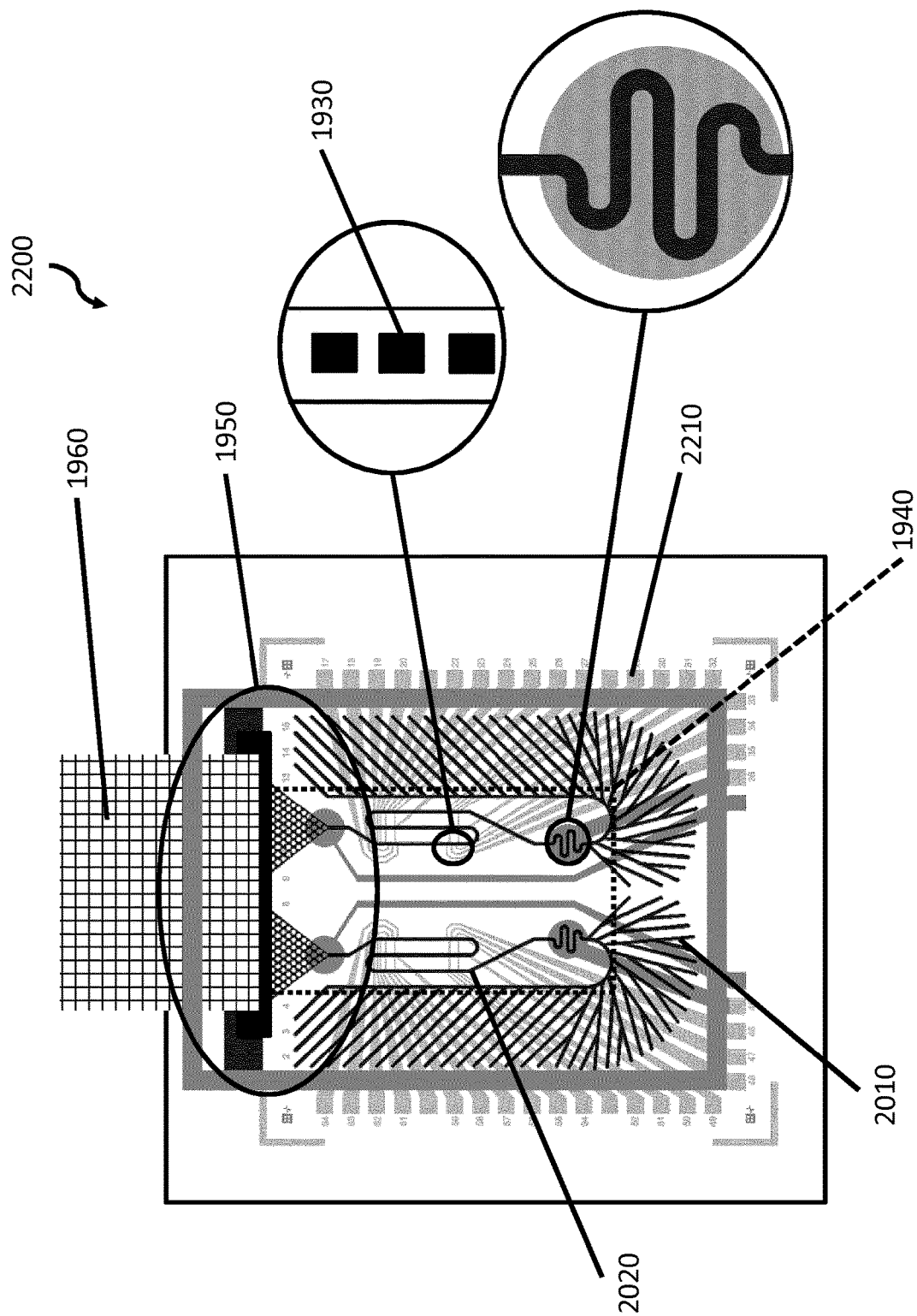
FIG. 22 is a schematic diagram of a system for collection and analysis of a fluid from a surface, according to an illustrative embodiment.

FIG. 22 shows another illustrative example of a system 2200 that can be integrated on a microchip. System 2200 includes a collection and delivery module, a flow regulation module and a waste module similar to system 2000 shown in FIG. 20, with two groups of arborescent collection structures 2010 and microfluidic delivery channel 2020. An optional lid 1940 can locally close the channels if needed. System 2200 can also include a flow regulation module 1950 with a capillary pump and a hydrophobic barrier. A waste module 1960 with a wicking strip and an absorbent pad can be used to collect and dispose of the fluid. System 2200 also includes a main sensor module similar to module 1400 shown in FIG. 14. In addition, system 2200 includes electrical connections 2210 to connect the sensors with an electronic circuit which can provide power to the sensors and collect measurement data from the sensors. For example, electrical connections 2210 can include pads connected to an electronic circuit via wire bonding, solder balls, etc.

The microchip or microchip assembly may be integrated on a printed-circuit board (PCB) e.g., a flex PCB). The PCB may be incorporated into a portable electronic device such as a patch, a wristband device, a watch, a smartphone, or a tablet computer.

Figure 23:
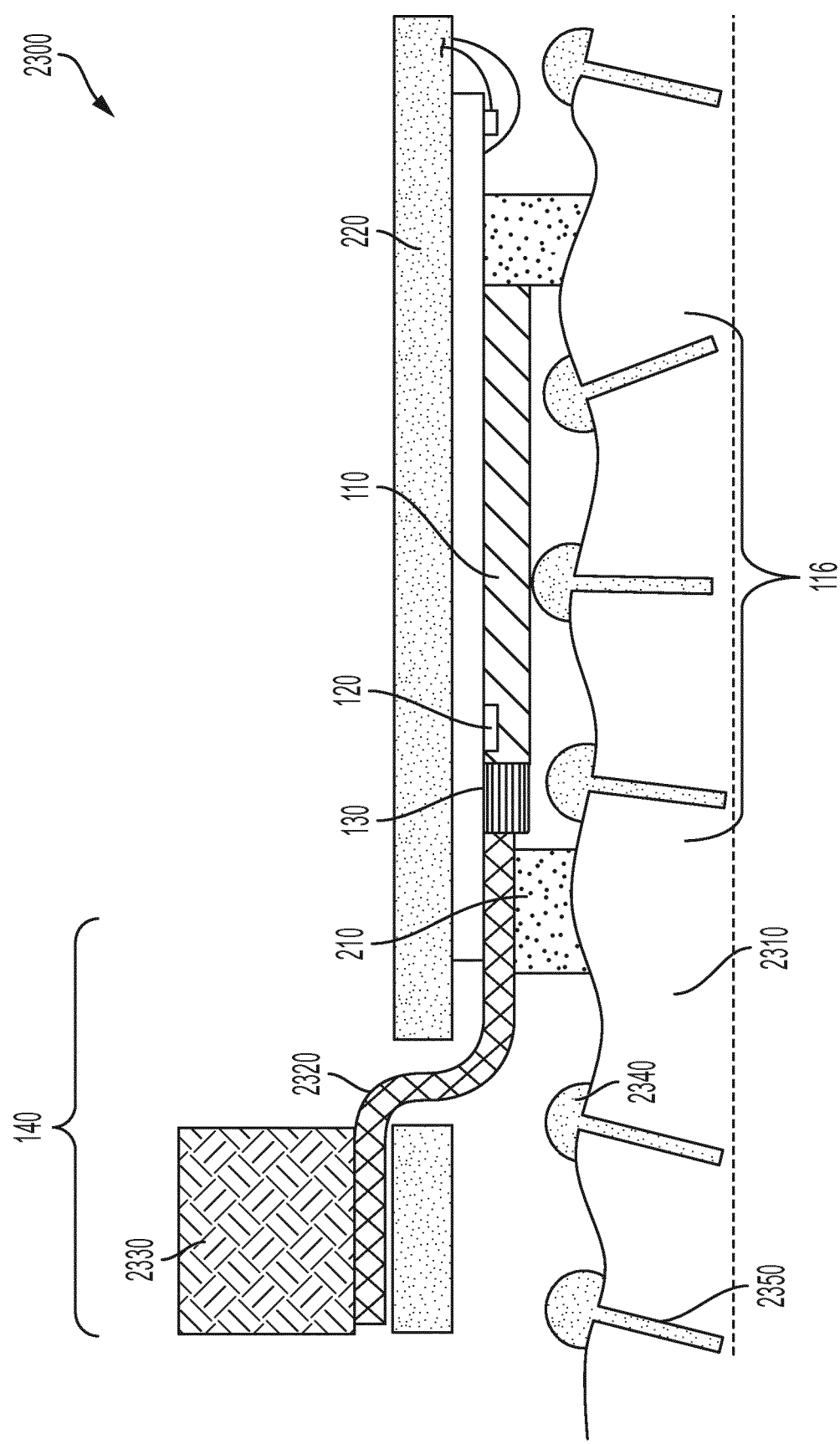
FIG. 23 is a schematic diagram showing integration of a system for collection and analysis of a fluid from a surface within a flexible PCB and a patch for measurements on skin, according to an illustrative embodiment.

The system can be used for sweat collection and analysis when placed on human skin. FIG. 23 shows an illustrative example of a system 2300, embedded in a patch that is affixed to the human body 2310 with a skin adhesive. The system can be fabricated or disposed on a flexible substrate (e.g., a flex PCB). A collection zone 116 is defined by the surrounding sealant 210. In addition to collection and delivery module 110, main sensor module 120, flow regulation module 130, the system can include a waste module 140 with a wicking strip 2320 and an absorbent pad 2330. Sweat droplets 2340 coming from sweat ducts 2350 within the collection zone 116 can be collected by the collection and delivery module 110 and transported to the main sensor module 120 for detection and analysis.

Figure 24:
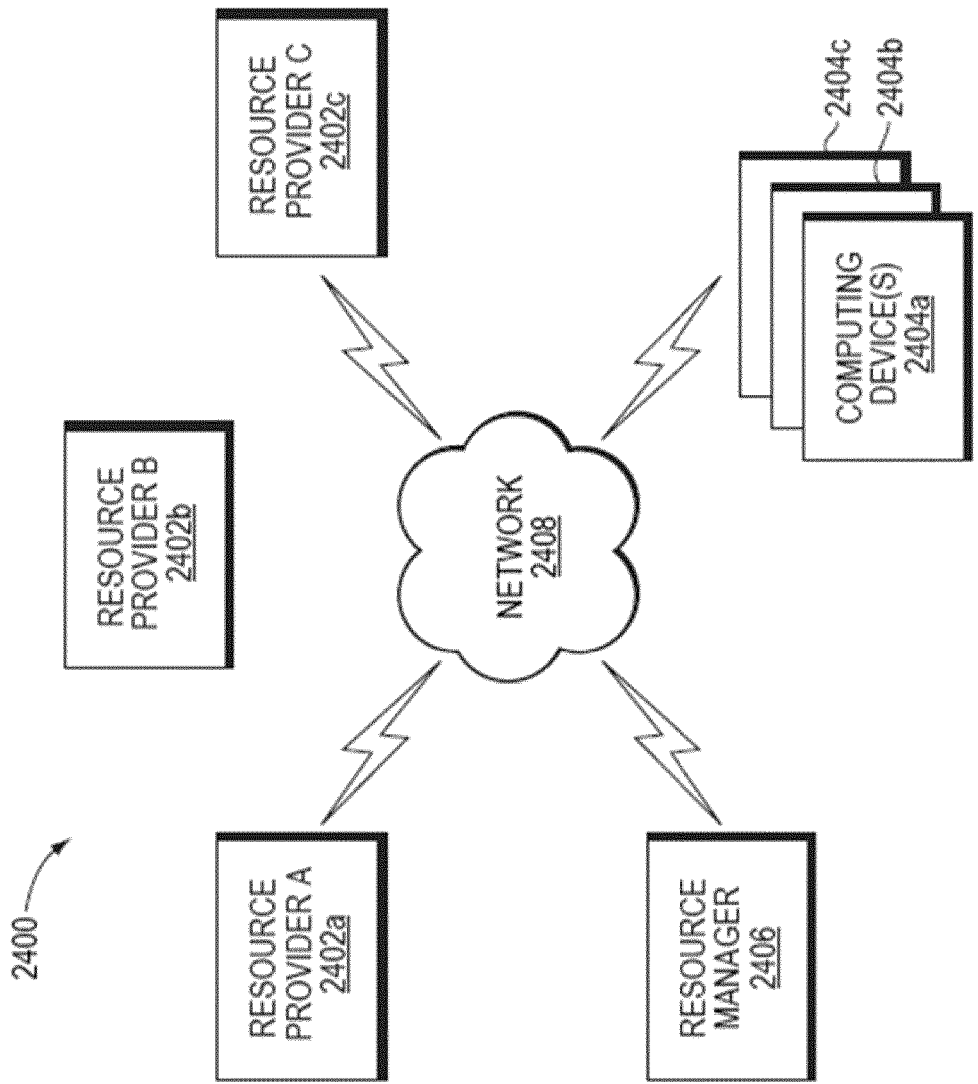
FIG. 24 is a block diagram of an example network environment for use in the methods and systems described herein, according to an illustrative embodiment.

As shown in FIG. 24, an implementation of a network environment 2400 for use in the systems, methods, and architectures described herein, is shown and described. In brief overview, referring now to FIG. 24, a block diagram of an exemplary cloud computing environment 2400 is shown and described. The cloud computing environment 2400 may include one or more resource providers 2402a, 2402b, 2402c (collectively, 2402). Each resource provider 2402 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 2402 may be connected to any other resource provider 2402 in the cloud computing environment 2400. In some implementations, the resource providers 2402 may be connected over a computer network 2408. Each resource provider 2402 may be connected to one or more computing device 2404a, 2404b, 2404c (collectively, 2404), over the computer network 2408.

The cloud computing environment 2400 may include a resource manager 2406. The resource manager 2406 may be connected to the resource providers 2402 and the computing devices 2404 over the computer network 2408. In some implementations, the resource manager 2406 may facilitate the provision of computing resources by one or more resource providers 2402 to one or more computing devices 2404. The resource manager 2406 may receive a request for a computing resource from a particular computing device 2404. The resource manager 2406 may identify one or more resource providers 2402 capable of providing the computing resource requested by the computing device 2404. The resource manager 2406 may select a resource provider 2402 to provide the computing resource. The resource manager 2406 may facilitate a connection between the resource provider 2402 and a particular computing device 2404. In some implementations, the resource manager 2406 may establish a connection between a particular resource provider 2402 and a particular computing device 2404. In some implementations, the resource manager 2406 may redirect a particular computing device 2404 to a particular resource provider 2402 with the requested computing resource.

Figure 25:
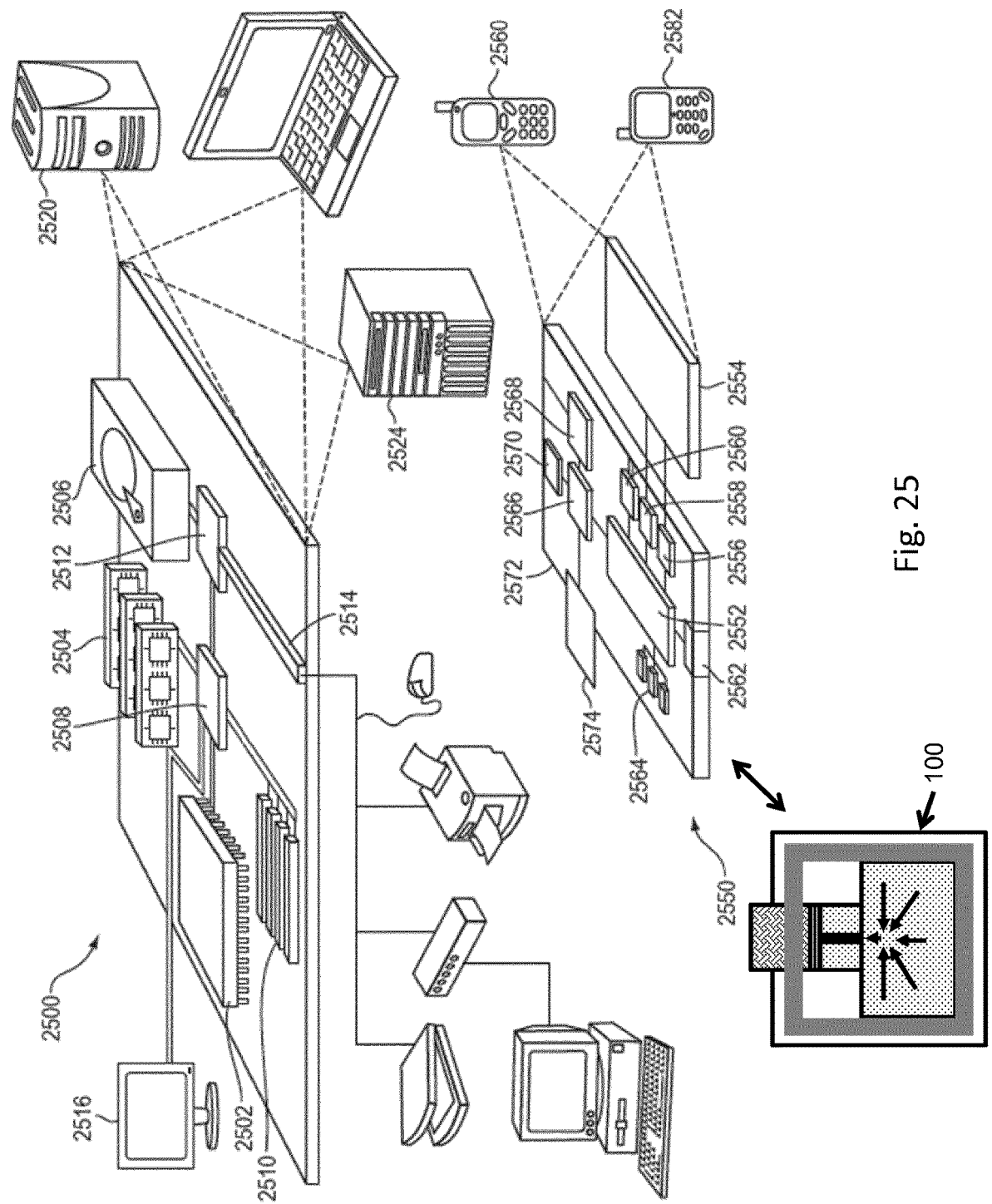
FIG. 25 is a block diagram of an example computing device and an example mobile computing device, for use in illustrative embodiments of the invention.

FIG. 25 shows an example of a computing device 2500 and a mobile computing device 2550 that can be used in the methods and systems described in this disclosure. For example, the computing device 2500 and/or mobile computing device 2550 can be in electronic communication with a system 100 for collecting and analyzing a fluid, as described. The computing device 2500 is intended to represent various forms of digital computers, such as laptops, desktops, workstations, personal digital assistants, servers, blade servers, mainframes, and other appropriate computers. The mobile computing device 2550 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 2500 includes a processor 2502, a memory 2504, a storage device 2506, a high-speed interface 2508 connecting to the memory 2504 and multiple high-speed expansion ports 2510, and a low-speed interface 2512 connecting to a low-speed expansion port 2514 and the storage device 2506. Each of the processor 2502, the memory 2504, the storage device 2506, the high-speed interface 2508, the high-speed expansion ports 2510, and the low-speed interface 2512, are interconnected using various busses, and may be mounted on a common motherboard or in other manners as appropriate. The processor 2502 can process instructions for execution within the computing device 2500, including instructions stored in the memory 2504 or on the storage device 2506 to display graphical information for a GUI on an external input/output device, such as a display 2516 coupled to the high-speed interface 2508. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system). Thus, as the term is used herein, where a plurality of functions are described as being performed by "a processor", this encompasses embodiments wherein the plurality of functions are performed by any number of processors (one or more) of any number of computing devices (one or more). Furthermore, where a function is described as being performed by "a processor", this encompasses embodiments wherein the function is performed by any number of processors (one or more) of any number of computing devices (one or more) (e.g., in a distributed computing system).

The memory 2504 stores information within the computing device 2500. In some implementations, the memory 2504 is a volatile memory unit or units. In some implementations, the memory 2504 is a non-volatile memory unit or units. The memory 2504 may also be another form of computer-readable medium, such as a magnetic or optical disk.

The storage device 2506 is capable of providing mass storage for the computing device 2500. In some implementations, the storage device 2506 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 2502), perform one or more methods, such as those described above. The instructions can also be stored by one or more storage devices such as computer- or machine-readable mediums (for example, the memory 2504, the storage device 2506, or memory on the processor 2502).

The high-speed interface 2508 manages bandwidth-intensive operations for the computing device 2500, while the low-speed interface 2512 manages lower bandwidth-intensive operations. Such allocation of functions is an example only. In some implementations, the high-speed interface 2508 is coupled to the memory 2504, the display 2516 (e.g., through a graphics processor or accelerator), and to the high-speed expansion ports 2510, which may accept various expansion cards (not shown). In the implementation, the low-speed interface 2512 is coupled to the storage device 2506 and the low-speed expansion port 2514. The low-speed expansion port 2514, which may include various communication ports (e.g., USB, BLUETOOTH®, Ethernet, wireless Ethernet) may be coupled to one or more input/output devices, such as a keyboard, a pointing device, a scanner, or a networking device such as a switch or router, e.g., through a network adapter.

The computing device 2500 may be implemented in a number of different forms, as shown in the figure. For example, it may be implemented as a standard server 2520, or multiple times in a group of such servers. In addition, it may be implemented in a personal computer such as a laptop computer 2522. It may also be implemented as part of a rack server system 2524. Alternatively, components from the computing device 2500 may be combined with other components in a mobile device (not shown), such as a mobile computing device 2550. Each of such devices may contain one or more of the computing device 2500 and the mobile computing device 2550, and an entire system may be made up of multiple computing devices communicating with each other.

The mobile computing device 2550 includes a processor 2552, a memory 2564, an input/output device such as a display 2554, a communication interface 2566, and a transceiver 2568, among other components. The mobile computing device 2550 may also be provided with a storage device, such as a micro-drive or other device, to provide additional storage. Each of the processor 2552, the memory 2564, the display 2554, the communication interface 2566, and the transceiver 2568, are interconnected using various buses, and several of the components may be mounted on a common motherboard or in other manners as appropriate.

The processor 2552 can execute instructions within the mobile computing device 2550, including instructions stored in the memory 2564. The processor 2552 may be implemented as a chipset of chips that include separate and multiple analog and digital processors. The processor 2552 may provide, for example, for coordination of the other components of the mobile computing device 2550, such as control of user interfaces, applications run by the mobile computing device 2550, and wireless communication by the mobile computing device 2550.

The processor 2552 may communicate with a user through a control interface 2558 and a display interface 2556 coupled to the display 2554. The display 2554 may be, for example, a TFT (Thin-Film-Transistor Liquid Crystal Display) display or an OLED (Organic Light Emitting Diode) display, or other appropriate display technology. The display interface 2556 may comprise appropriate circuitry for driving the display 2554 to present graphical and other information to a user. The control interface 2558 may receive commands from a user and convert them for submission to the processor 2552. In addition, an external interface 2562 may provide communication with the processor 2552, so as to enable near area communication of the mobile computing device 2550 with other devices. The external interface 2562 may provide, for example, for wired communication in some implementations, or for wireless communication in other implementations, and multiple interfaces may also be used.

The memory 2564 stores information within the mobile computing device 2550. The memory 2564 can be implemented as one or more of a computer-readable medium or media, a volatile memory unit or units, or a non-volatile memory unit or units. An expansion memory 2574 may also be provided and connected to the mobile computing device 2550 through an expansion interface 2572, which may include, for example, a SIMM (Single In Line Memory Module) card interface or a DIMM (Double In Line Memory Module) card interface. The expansion memory 2574 may provide extra storage space for the mobile computing device 2550, or may also store applications or other information for the mobile computing device 2550. Specifically, the expansion memory 2574 may include instructions to carry out or supplement the processes described above, and may include secure information also. Thus, for example, the expansion memory 2574 may be provided as a security module for the mobile computing device 2550, and may be programmed with instructions that permit secure use of the mobile computing device 2550. In addition, secure applications may be provided via the DIMM cards, along with additional information, such as placing identifying information on the DIMM card in a non-hackable manner.

The memory may include, for example, flash memory and/or NVRAM memory (non-volatile random access memory), as discussed below. In some implementations, instructions are stored in an information carrier and, when executed by one or more processing devices (for example, processor 2552), perform one or more methods, such as those described above. The instructions can also be stored by one or more storage devices, such as one or more computer- or machine-readable mediums (for example, the memory 2564, the expansion memory 2574, or memory on the processor 2552). In some implementations, the instructions can be received in a propagated signal, for example, over the transceiver 2568 or the external interface 2562.

The mobile computing device 2550 may communicate wirelessly through the communication interface 2566, which may include digital signal processing circuitry where necessary. The communication interface 2566 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 2568 using a radio-frequency. In addition, short-range communication may occur, such as using a BLUETOOTH®, WI-FI®, or other such transceiver (not shown). In addition, a GPS (Global Positioning System) receiver module 2570 may provide additional navigation- and location-related wireless data to the mobile computing device 2550, which may be used as appropriate by applications running on the mobile computing device 2550.

The mobile computing device 2550 may also communicate audibly using an audio codec 2560, which may receive spoken information from a user and convert it to usable digital information. The audio codec 2560 may likewise generate audible sound for a user, such as through a speaker, e.g., in a handset of the mobile computing device 2550. Such sound may include sound from voice telephone calls, may include recorded sound (e.g., voice messages, music files, etc.) and may also include sound generated by applications operating on the mobile computing device 2550.

The mobile computing device 2550 may be implemented in a number of different forms, as shown in the figure. For example, it may be implemented as a cellular telephone 2580. It may also be implemented as part of a smart-phone 2582, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In some implementations, the modules (e.g. data aggregation module 2530, mapping module 2550, specifications module 2570) described herein can be separated, combined or incorporated into single or combined modules. The modules depicted in the figures are not intended to limit the systems described herein to the software architectures shown therein.

Testing Environment Setup

Figure 26:
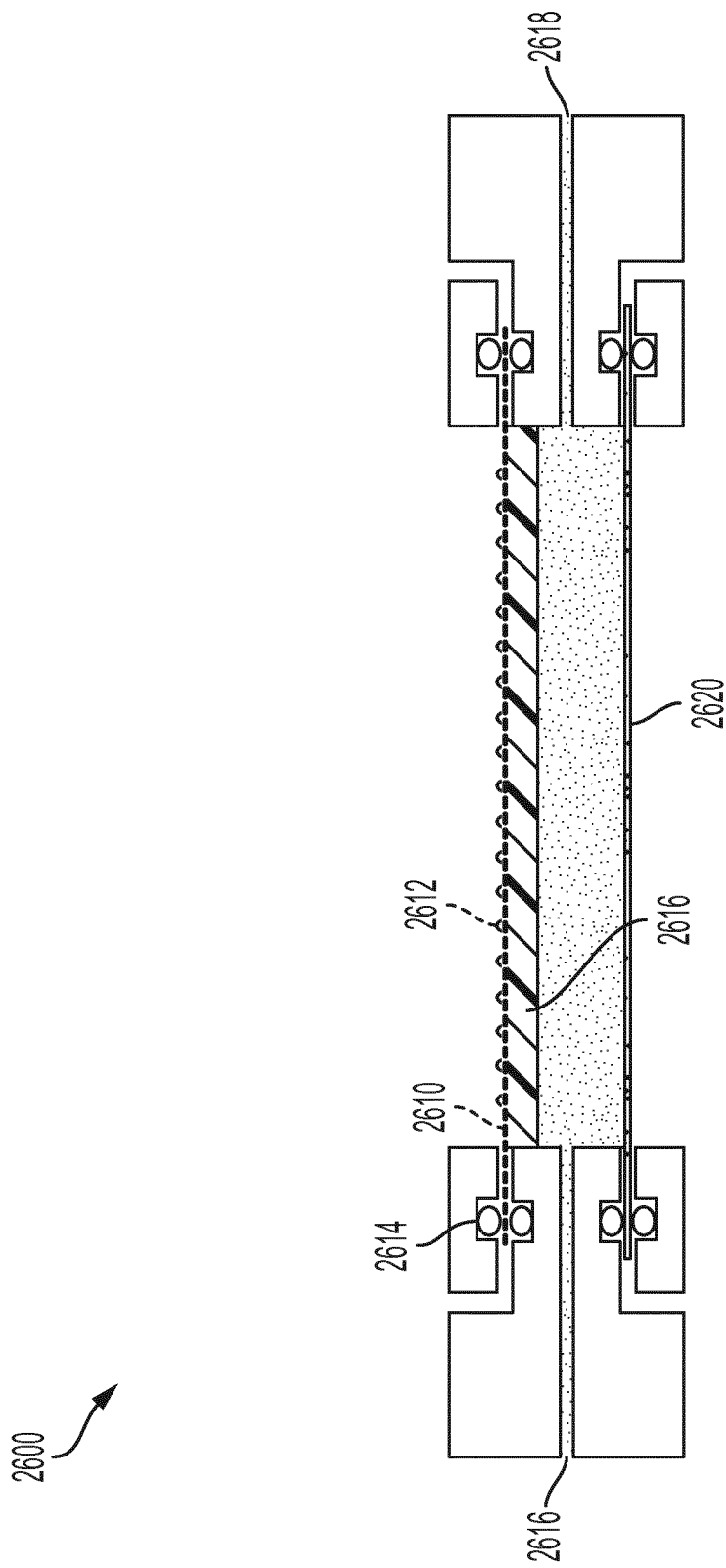
FIG. 26 is a schematic diagram representing a cross-sectional view of a system to homogenously dispense liquid on the surface of a porous membrane (e.g., to mimic sweating on skin), according to an illustrative embodiment.

FIG. 26 is a schematic diagram of a device 2600 for mimicking the surface of skin (e.g., a wet surface). The performance of the biofluid collection and analysis system described herein can also be tested with this setup. The surface (e.g., a wet surface) may be a porous membrane 2610. The membrane may be a foil or a laminate, such as a polymer foil (e.g., PET, polycarbonate, polyimide, PDMS, or the like) or a metal foil (e.g., an aluminum, copper, or steel foil) that includes pores 2612. Pores 2612 can be patterned, for example, by cutting (e.g., laser-cutting), by machining (e.g., drilling or milling), by imprinting, etching (e.g., chemical etching, reactive-ion etching), and/or molding. Membrane 2610 may be mounted in a setup with O-ring 2614 such that a liquid is dispensed homogeneously (e.g., evenly) among a portion (up to all) of pores 2612. This can be achieved by inserting a material of higher fluidic resistance 2616 than pores 2612 on the backside of membrane 2610. This resistive material 2616 can be, for example, a hydrogel layer.

Still referring to FIG. 26, the surface (e.g., collection surface 118) may be a porous membrane 2610 designed to mimic sweating on skin, and therefore to reproduce some or all of the characteristics of human skin, such as pore (or sweat duct) density, pore (or sweat duct) size, hydrophobicity, roughness, patterning (e.g., the patterned "v-groove" network of skin), elasticity, the presence of a lipidic film, etc. A setup to fluidically connect such a membrane and mount it on a microscope may be used as a model to characterize, develop, and optimize the biofluid collection structures described herein. The performance of the biofluid collection and analysis system described herein can also be tested with this setup.

In certain embodiments, system 2600 includes an inlet 2616 for introducing a testing fluid into the system and an outlet 2618. System 2600 can also include a glass window 2620 for monitoring the flow distribution of the testing fluid within the system.

Elements of different implementations described herein may be combined to form other implementations not specifically set forth above. Elements may be left out of the processes, computer programs, databases, etc. described herein without adversely affecting their operation. In addition, the logic flows depicted in the figures do not require the particular order shown, or sequential order, to achieve desirable results. Various separate elements may be combined into one or more individual elements to perform the functions described herein. In view of the structure, functions and apparatus of the systems and methods described here, in some implementations.

The various described embodiments of the invention may be used in conjunction with one or more other embodiments unless technically incompatible.

While the invention has been particularly shown and described with reference to specific preferred embodiments, it should be understood by those skilled in the art that various changes in form and detail may be made therein without departing from the spirit and scope of the invention as defined by the appended claims.

The invention claimed is:

1. A system for collection and analysis of a biofluid from skin, the system comprising:
    a collection and delivery module;
    a sensing module;
    a passive flow regulation module; and
    a waste module,
    wherein (i) the collection and delivery module collects the biofluid from the skin and transports the biofluid to the sensing module, (ii) the sensing module determines one or more chemical and/or physical properties of the biofluid, (iii) the flow regulation module controls flow of the biofluid through the system, and (iv) the waste module collects and disposes of the biofluid after the analysis is complete, and wherein the passive flow regulation module comprises a surface property barrier and a capillary pump disposed after the surface property barrier along a direction of flow of the biofluid through the system and wherein the flow regulation module is positioned between the sensing module and the waste module along the direction of flow.

2. The system of claim 1, comprising a wetting sensor module for detecting presence of the biofluid, wherein the wetting sensor module comprises a conductivity sensor.

3. The system of claim 1, comprising a microchip assembly for integrating at least one module selected from the group consisting of the collection and delivery module, the sensing module, the flow regulation module, and the waste module, wherein the microchip assembly comprises a printed circuit board or a wearable device.

4. The system of claim 1, wherein the collection and delivery module comprises a surface with one or more collection structures.

5. The system of claim 4, wherein the collection structures comprise at least one fluidic channel or a fluidic channel network.

6. The system of claim 5, wherein the at least one fluidic channel or fluidic channel network comprises a member selected from the group consisting of a groove, an open or closed microfluidic channel, a two-dimensional channel defined by surface property contrast, and a channel made of a fixed gel matrix permeable to a biofluid.

7. The system of claim 5, wherein each of the at least one fluidic channel or fluidic channel network is modified by physical and/or chemical treatments.

8. The system of claim 5, wherein a portion of the at least one fluidic channel or fluidic channel network comprises pillar structures to facilitate biofluid transport via capillary action.

9. The system of claim 8, wherein the pillar structures comprise an interstitial distance gradient in one direction to promote directional flow.

10. The system of claim 5, wherein the at least one fluidic channel or fluidic channel network comprises a filter to exclude a contaminant.

11. The system of claim 4, comprising a sealant material surrounding the one or more collection structures.

12. The system of claim 11, wherein the sealant material is impermeable to liquid.

13. The system of claim 11, wherein the sealant material comprises a member selected from the group consisting of an elastomer, a gel, a grease, a glue, an adhesive, and a laminate.

14. The system of claim 4, wherein the one or more collection structures comprise an arborescent channel network, and wherein the arborescent channel network comprises a plurality of branched channels.

15. The system of claims 1, wherein the sensing module comprises at least one sensor for measuring one or more chemical and/or physical properties of the biofluid, wherein the one or more chemical and/or physical properties of the biofluid comprise a member selected from the group consisting of: a concentration of one or more substances present in the biofluid, a pH value of the biofluid, a conductivity of the biofluid, a temperature of the biofluid and/or the skin, a pressure of the biofluid, and a flow rate of the biofluid.

16. The system of claim 15, wherein the sensing module comprises one or more reference electrodes.

17. The system of claim 1, wherein the waste module comprises a capillary pump and a waste reservoir.

18. The system of claim 2, wherein the conductivity sensor comprises one or more electrodes.

19. The system of claim 18, wherein the one or more electrodes are actuated by an AC signal in a frequency range of about 1 kHz to about 100 kHz.

20. The system of claim 18, wherein the one or more electrodes are actuated by a DC signal.

21. A method of using the system of claim 1 for collection and analysis of a biofluid from skin, the method comprising affixing the system to a human body.

22. The system of claim 1, wherein the surface property barrier is a hydrophobic barrier.

* * * * *